(12) United States Patent
Marin et al.

(10) Patent No.: US 7,514,510 B2
(45) Date of Patent: *Apr. 7, 2009

(54) FLUORENYL CATALYST COMPOSITIONS AND OLEFIN POLYMERIZATION PROCESS

(75) Inventors: Vladimir Marin, Houston, TX (US); Abbas Razavi, Mons (BE)

(73) Assignee: Fina Technology, Inc., Houston, TX (US)

( * ) Notice: Subject to any disclaimer, the term of this patent is extended or adjusted under 35 U.S.C. 154(b) by 45 days.

This patent is subject to a terminal disclaimer.

(21) Appl. No.: 11/459,801

(22) Filed: Jul. 25, 2006

(65) Prior Publication Data
US 2008/0027189 A1   Jan. 31, 2008

(51) Int. Cl.
*C08F 4/76* (2006.01)
*C08F 4/64* (2006.01)

(52) U.S. Cl. .................. 526/170; 526/160; 526/943; 526/941; 526/351; 526/352; 526/348

(58) Field of Classification Search ................ 526/170, 526/160, 943, 348
See application file for complete search history.

(56) References Cited

U.S. PATENT DOCUMENTS

| | | | |
|---|---|---|---|
| 4,271,060 A | 6/1981 | Hubby | |
| 4,404,344 A | 9/1983 | Sinn et al. | |
| 4,543,399 A | 9/1985 | Jenkins, III et al. | |
| 4,588,790 A | 5/1986 | Jenkins, III et al. | |
| 4,767,735 A | 8/1988 | Ewen et al. | |
| 5,001,205 A | 3/1991 | Hoel | |
| 5,028,670 A | 7/1991 | Chinh et al. | |
| 5,155,080 A | 10/1992 | Elder et al. | |
| 5,236,998 A | 8/1993 | Lundeen et al. | |
| 5,317,036 A | 5/1994 | Brady, III et al. | |
| 5,352,749 A | 10/1994 | DeChellis et al. | |
| 5,405,922 A | 4/1995 | DeChellis et al. | |
| 5,436,304 A | 7/1995 | Griffin et al. | |
| 5,462,999 A | 10/1995 | Griffin et al. | |
| 5,525,678 A | 6/1996 | Mink et al. | |
| 5,589,555 A | 12/1996 | Zboril et al. | |
| 5,616,661 A | 4/1997 | Eisinger et al. | |
| 5,627,242 A | 5/1997 | Jacobsen et al. | |
| 5,643,847 A | 7/1997 | Walzer, Jr. | |
| 5,665,818 A | 9/1997 | Tilston et al. | |
| 5,668,228 A | 9/1997 | Chinh et al. | |
| 5,677,375 A | 10/1997 | Rifi et al. | |
| 6,002,033 A * | 12/1999 | Razavi et al. ................ 556/11 |
| 6,143,686 A | 11/2000 | Vizzini et al. | |
| 6,147,173 A | 11/2000 | Holtcamp | |
| 6,180,735 B1 | 1/2001 | Wenzel | |
| 6,207,606 B1 | 3/2001 | Lue et al. | |
| 6,211,105 B1 | 4/2001 | Holtcamp | |
| 6,228,795 B1 | 5/2001 | Vizzini | |
| 6,242,545 B1 | 6/2001 | Jejelowo et al. | |
| 6,245,705 B1 | 6/2001 | Kissin | |
| 6,245,868 B1 | 6/2001 | Agapiou et al. | |
| 6,248,845 B1 | 6/2001 | Loveday et al. | |
| 6,271,323 B1 | 8/2001 | Loveday et al. | |
| 6,274,684 B1 | 8/2001 | Loveday et al. | |
| 6,300,436 B1 | 10/2001 | Agapiou et al. | |
| 6,339,134 B1 | 1/2002 | Crowther et al. | |
| 6,340,730 B1 | 1/2002 | Murray et al. | |
| 6,346,586 B1 | 2/2002 | Agapiou et al. | |
| 6,359,072 B1 | 3/2002 | Whaley | |
| 6,380,328 B1 | 4/2002 | McConville et al. | |
| 6,420,580 B1 | 7/2002 | Holtcamp et al. | |
| 7,034,157 B2 | 4/2006 | Razavi et al. | |
| 7,094,938 B1 | 8/2006 | Marin et al. | |
| 2005/0148460 A1 | 7/2005 | Marin et al. | |

FOREIGN PATENT DOCUMENTS

WO   WO 2004/020481 A1 *   3/2004

OTHER PUBLICATIONS

Alt, H.G.; Zenk, R. J. Organomet. Chem. 1996, 526, 295-301.*
Alt, H.G.; Zenk, R. J. Organomet. Chem. 1996, 518, 7-15.*
Koppl, A.; Babel, A. I.; Alt, H. G. J. Mol. Catal. A: Chemical 2000, 153, 109-119.*
Fan, W., et al., "Alternating Stereospecific Copolymerization of Ethylene and Propylene with Metallocene Catalysts,"J. Am. Chem. Soc., vol. 123, 2001, American Chemical Society, pp. 9555-9563.
Hlatky, Gregory G., "Heterogeneous Single Site Catalysts for Olefin Polymerization," Chemical Reviews, vol. 100, 2000, American Chemical Society, pp. 1347-1376.
Jin, Jizhu, et al., "Alternating copolymerization of ethylene and propene with the [ethylene(1-indenyl) (9-fluorenyl)]zirconium dichloride-methylaluminoxane catalyst system," Macromol. Rapid Commun., vol. 19, 1998, Hüthig & Wepf Verlag, Zug, pp. 337-339.
Leclerc, Margarete K., et al., "Alternating Ethene/Propene Copolymerization with a Metallocene Catalyst**," Angew. Chem. Int. Ed., vol. 37, No. 7, 1998, Wiley-VCH Verlag GmbH, D-69451 Weinheim, pp. 922-925.
U.S. Appl. No. 11/305,704, filed on Dec. 16, 2005, entitled "Catalyst Compositions and Methods of Forming Isotactic Polypropylene."
U.S. Appl. No. 11/205,934, filed on Aug. 17, 2005, entitled "Preparation and Use of Tetrasubstituted Fluorenyl Catalysts for Polymerization of Olefins."

* cited by examiner

*Primary Examiner*—Vasu Jagannathan
*Assistant Examiner*—Rip A. Lee
(74) *Attorney, Agent, or Firm*—Diane L. Kilpatrick-Lee; Rodney Carroll

(57) ABSTRACT

An olefin polymerization process comprising contacting one or more olefins and a catalyst component in a reaction zone under suitable reaction conditions to form a polyolefin, wherein the catalyst component is characterized by the formula:

$$B(Cp)(Fl)MQ_2$$

wherein M comprises a metal, Q comprises a halogen, an alkyl group or an aryl group or combinations thereof, Cp comprises a cyclopentadienyl group, Fl comprises a fluorenyl group, B is a bridging group that may be characterized by the general formula —YRH wherein Y comprises C or Si and R comprises an alkyl group, an aryl group, a poly-aryl group or combinations thereof.

10 Claims, 22 Drawing Sheets

FLUORENYL CATALYST COMPOSITIONS AND OLEFIN POLYMERIZATION PROCESS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

1. Technical Field

This disclosure relates to catalyst systems for olefin polymerization. More specifically, this disclosure relates to metallocene catalyst systems and polymers produced therefrom.

2. Background

Olefin polymers and copolymers such as polyethylene, polypropylene and ethylene-propylene can be produced under various polymerization conditions and employing various polymerization catalysts. In the case of $C_3$ or greater alpha olefins, the resulting polymer may exhibit stereoregularity. For example, in the case of propylene, a polypropylene product may be isotactic wherein each methyl group attached to the tertiary carbon atoms of the successive monomeric unit falls on the same side of a hypothetical plane through the main chain of the polymer. Polypropylene may also be syndiotactic wherein the methyl groups attached to the tertiary carbon atoms of the successive monomeric unit are arranged as racemic dyads. In other words, the methyl groups in isotactic polypropylene lie on the same side of the polymer backbone whereas in syndiotactic polypropylene the methyl groups lie on alternate sides of the polymer backbone. In the absence of any regular arrangement of the methyl groups with respect to the polymer backbone the polymer is atactic. The stereoregularity of the polymeric product impacts both the physical and mechanical properties of said product.

Fluorenyl-type metallocene catalysts are effective catalysts in the polymerization of olefin polymers such as ethylene, propylene and higher olefins or other ethylenically unsaturated monomers into homopolymers or copolymers. Fluorenyl-type metallocenes are generally characterized by bridged cyclopentadienyl and fluorenyl groups that serve as a ligand to a metal atom. Varying the substituents or position of substituents on the fluorenyl group, cyclopentadienyl group or bridging moiety of a given fluorenyl-type metallocene catalyst may produce polymers having very different physical properties. For example, an isomer of a fluorenyl-type metallocene catalyst may produce isotactic polypropylene, while another isomer of the catalyst may produce syndiotactic polypropylene. In addition, properties such as the molecular weight and melting points of the polypropylene composition may vary and as a result the mechanical properties and utility of the polymer may vary.

Thus, there is an ongoing need for catalysts capable of producing stereoregular polypropylene compositions with differing physical properties such as molecular weight and melting points.

BRIEF SUMMARY OF SOME OF THE EMBODIMENTS

Disclosed herein is an olefin polymerization process comprising contacting one or more olefins and a catalyst component in a reaction zone under suitable reaction conditions to form a polyolefin, wherein the catalyst component is characterized by the formula:

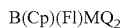

$$B(Cp)(Fl)MQ_2$$

wherein M comprises a metal, Q comprises a halogen, an alkyl group or an aryl group or combinations thereof, Cp comprises a cyclopentadienyl group, Fl comprises a fluorenyl group, B is a bridging group that may be characterized by the general formula —YRH wherein Y comprises C or Si and R comprises an alkyl group, an aryl group, a poly-aryl group or combinations thereof.

The foregoing has outlined rather broadly the features and technical advantages of the present disclosure in order that the detailed description of the embodiments that follows may be better understood. Additional features and advantages of the embodiments will be described hereinafter that form the subject of the claims of the disclosure. It should be appreciated by those skilled in the art that the conception and the specific embodiments disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims.

DETAILED DESCRIPTION OF THE EMBODIMENTS

Figure 1:
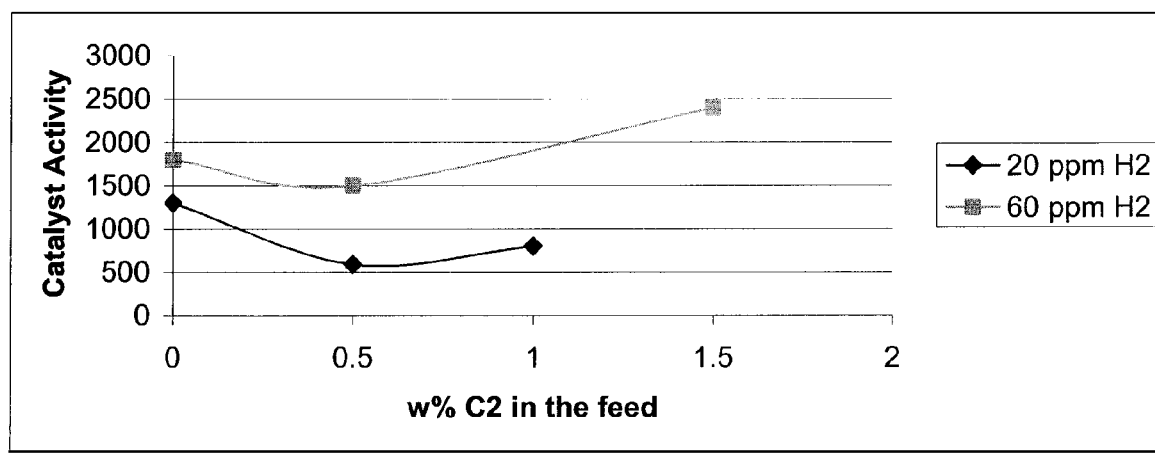
FIG. 1 is a plot of catalyst activity versus ethylene concentration in feed.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

The term "activity" generally refers to the weight of product produced per weight of the catalyst used in a process per hour of reaction at a standard set of conditions (e.g., grams product/gram catalyst/hr).

The term "substituted" refers to an atom, radical or group replacing hydrogen in a chemical compound.

The term "homogenous polymerization" refers to polymerization via contact with a catalyst that is present within the reaction system in the same phase as the reactants (e.g., a catalyst in solution within a liquid phase reaction.)

The term "tacticity" refers to the arrangement of pendant groups in a polymer. For example, a polymer is "atactic" when its pendant groups are arranged in a random fashion on both sides of the chain of the polymer. In contrast, a polymer is "isotactic" when all of its pendant groups are arranged on the same side of the chain and "syndiotactic" when its pendant groups alternate on opposite sides of the chain.

As used herein, "isotacticity" is measured via $^{13}C$ NMR spectroscopy using meso pentads and is expressed as percentage of meso pentads (% mmmm). As used herein, the term "meso pentads" refers to successive methyl groups located on the same side of the polymer chain.

As used herein, "molecular weight distribution" is the ratio of the weight average molecular weight to the number average molecular weight (Mw/Mn) of a polymer and may also be referred to as the polydispersity index.

As used herein, "melting temperature" is measured by differential scanning calorimetry using a modified version of ASTM D 3418-99. Specifically, for a sample weighing between 5 and 10 g, the following standard test conditions involved heating the sample from 50° C. to 210° C. to erase the thermal history of the sample, followed by holding the sample at 210° C. for 5 minutes. The sample is then cooled to 50° C. to induce recrystallization and subsequently subjected to a second melt in the temperature range 50° C. to 190° C. For each of these temperature changes, the temperature is ramped at a rate of 10° C./min.

Disclosed herein are catalysts and catalyst systems for the polymerization of olefins. A catalyst system herein refers to one or more chemical agents, which operate in concert to increase the rate of a reaction. Said catalyst system may comprise a metallocene catalyst. Metallocene catalysts may be characterized generally as coordination compounds incorporating one or more cyclopentadienyl (Cp) groups (which may be substituted or unsubstituted, each substitution being the same or different) coordinated with a transition metal through π bonding.

In an embodiment, a catalyst for use in olefin polymerization comprises at least one cyclopentadienyl ligand, at least one fluorenyl ligand, at least one bridging ligand and at least one metal. These catalysts are collectively referred to herein as fluorenyl metallocene catalysts (FMC). Each of the components of the FMCs will be described in more detail herein. The FMC may be used in conjunction with one or more cocatalysts to produce a catalyst system that effects the polymerization of olefins such as alpha olefins to produce homopolymers or copolymers of said olefins. The disclosed catalysts may be employed in the production of stereoregular polymer products such as isotactic polypropylene.

In an embodiment a FMC for the polymerization of olefins may be represented by the general formula:

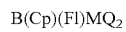

$$B(Cp)(Fl)MQ_2$$

where M comprises a metal, Q may comprise a halogen, an alkyl group, an aryl group, or combinations thereof, Cp is a cyclopentadienyl group, Fl is a fluorenyl group, and B is a structural bridge between Cp and Fl imparting stereorigidity to said catalyst. In some embodiments B, Q, Fl or any combination thereof may be substituted. In other embodiments B, Q, Fl or any combination thereof may be unsubstituted as will be described in detail later herein.

In an embodiment, a FMC for the polymerization of olefins comprises a cyclopentadienyl group (Cp). In an embodiment, the Cp group is unsubstituted, alternatively the Cp is substituted. In embodiments wherein the Cp group is substituted, the Cp group may have any number and/or placement of substituent groups capable of producing the desired polymer product. Unless otherwise specified, the substituents on the Cp may comprise an aliphatic group; an aromatic group; a cyclic group; any combination thereof or any substituted derivative thereof, including but not limited to, a halide, an alkoxide, or an amide-substituted derivative thereof; any one of which has from 1 to 20 carbon atoms; or hydrogen. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from one to 20 carbon atoms. Thus, aliphatic groups include, but are not limited to, hydrocarbyls such as paraffins and alkenyls. Cp substituent groups may be the same or different and may include hydrogen radicals, alkyls (e.g., methyl, ethyl, propyl, butyl (e.g., tert-butyl,) pentyl, hexyl, fluoromethyl, fluoroethyl, difluoroethyl, iodopropyl, bromohexyl, benzyl, phenyl, methylphenyl, tert-butylphenyl, chlorobenzyl, dimethylphosphine and methylphenylphosphine), alkenyls (e.g., 3-butenyl, 2-propenyl and 5-hexenyl), alkynyls, cycloalkyls (e.g., cyclopentyl and cyclohexyl), aryls (e.g., trimethylsilyl, trimethylgermyl, methyldiethylsilyl, acyls, aroyls, tris(trifluoromethyl)silyl, methylbis(difluoromethyl)silyl and bromomethyldimethylgermyl), alkoxys (e.g., methoxy, ethoxy, propoxy and phenoxy), aryloxys, alkylthiols, dialkylamines (e.g., dimethylamine and diphenylamine), alkylamidos, alkoxycarbonyls, aryloxycarbonyls, carbomoyls, alkyl- and dialkyl-carbamoyls, acyloxys, acylaminos, aroylaminos, organometalloid radicals (e.g., dimethylboron), Group 15 and Group 16 radicals (e.g., methylsulfide and ethylsulfide) and combinations thereof, for example. In a specific embodiment, the Cp group is mono-substituted in the 3 position with a tert-butyl group. In such an embodiment, the Cp group may or may not have further substitution.

In an embodiment, a FMC for the polymerization of olefins comprises a fluorenyl group (Fl). Fluorenyl groups may be characterized by the chemical formula and numbering scheme indicated in Formula (I):

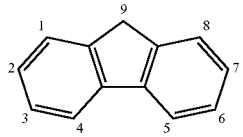

(I)

In this numbering scheme, 9 indicates the bridgehead carbon atom. The remaining carbon atoms available to accept substituents are indicated by numbers 1-4 on one phenyl group of the ligand, and numbers 5-8 on the other phenyl group of the fluorenyl ligand.

In an embodiment, the Fl group is unsubstituted, alternatively the Fl group is substituted. In embodiments wherein the Fl group is substituted, the Fl group may have any number and/or placement of substituent groups capable of producing the desired polymer product. Unless otherwise specified, the substituents on the Fl may comprise an aliphatic group; an aromatic group; a cyclic group; any combination thereof; any substituted derivative thereof, including but not limited to, a halide, an alkoxide, or an amide-substituted derivative thereof; any one of which has from 1 to 20 carbon atoms; or hydrogen. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from one to 20 carbon atoms. Thus, aliphatic groups include, but are not limited to, hydrocarbyls such as paraffins and alkenyls. Fl substituent groups may be the same or different and may include hydrogen radicals, alkyls (e.g., methyl, ethyl, propyl, butyl (e.g., tert-butyl), pentyl, hexyl, fluoromethyl, fluoroethyl, difluroethyl, iodopropyl, bromohexyl, benzyl, phenyl, methylphenyl, tert-butylphenyl, chlorobenzyl, dimethylphosphine and methylphenylphosphine), alkenyls (e.g., 3-butenyl, 2-propenyl and 5-hexenyl), alkynyls, cycloalkyls (e.g., cyclopentyl and cyclohexyl), aryls (e.g., trimethylsilyl, trimethylgermyl, methyldiethylsilyl, acyls, aroyls, tris(trifluoromethyl)silyl, methylbis(difluoromethyl)silyl and bromomethyldimethylgermyl), alkoxys (e.g., methoxy, ethoxy, propoxy and phenoxy), aryloxys, alkylthiols, dialkylamines (e.g., dimethylamine and diphenylamine), alkylamidos, alkoxycarbonyls, aryloxycarbonyls, carbomoyls, alkyl- and dialkyl-carbamoyls, acyloxys, acylaminos, aroylaminos, organometalloid radicals (e.g., dimethylboron), Group 15 and Group 16 radicals (e.g., methylsulfide and ethylsulfide) and combinations thereof, for example. In an embodiment, the Fl group is symmetrically disubstituted in the 3,6 positions, alternatively in the 2,7 positions. In such embodiments, the substituents may be an alkyl group, an aryl group or combinations thereof. In an embodiment, the Fl group is disubstituted at positions 3 and 6 with tert-butyl groups. In another embodiment, the Fl group is disubstituted at positions 2 and 7 with tert-butyl groups.

In an embodiment, a catalyst for the polymerization of olefins comprises a ligand (Y) which may be represented by chemical formula (II) below:

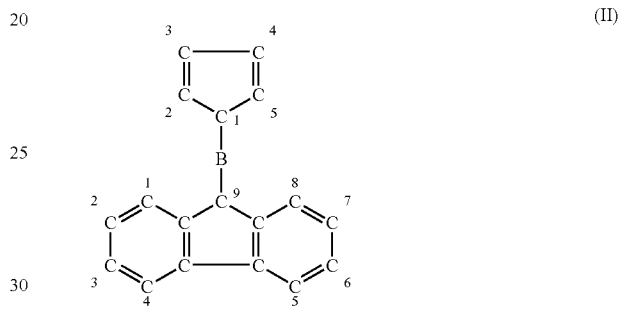

(II)

wherein a Cp group and a Fl group are structurally linked through a bridging group (B).

The Cp and Fl group may be of the type previously disclosed herein. B is a bridging group that may be characterized by the general formula —YRH wherein Y comprises C or Si and R comprises an alkyl group, an aryl group, a poly-aryl group or combinations thereof. In an embodiment, R is a poly-aryl group comprising at least two aryl groups, alternatively R is one of the compounds characterized by the chemical structures given in Group 1.

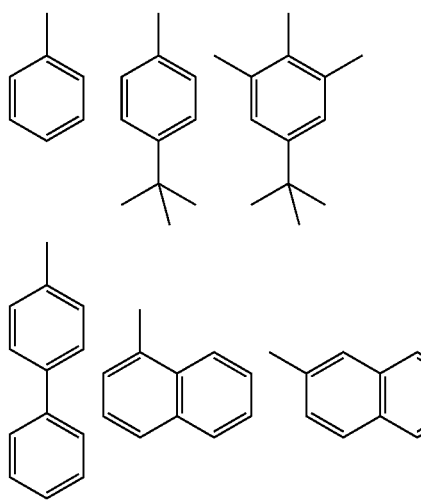

Group 1

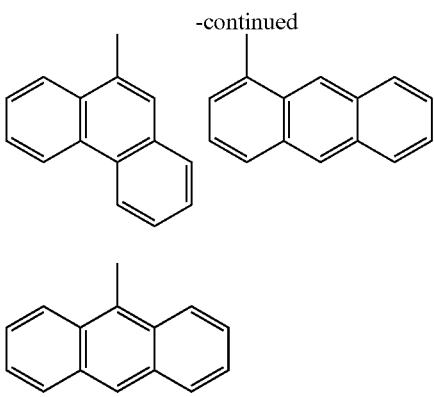

In an embodiment, a FMC for the polymerization of olefins comprises a metal (M). The metal atom "M" of the FMC, as described throughout the specification and claims, may comprise atoms of Groups 3 through 12 and lanthanide Group atoms, alternatively atoms of Groups 3 through 10, alternatively Sc, Ti, Zr, Hf, V, Nb, Ta, Mn, Re, Fe, Ru, Os, Co, Rh, Ir or Ni. Alternatively, M comprises zirconium, hafnium, or titanium. Alternatively, M comprises zirconium.

The oxidation state of the metal atom "M" may range from 0 to +7 or is +1, +2, +3, +4 or +5, for example. The groups bound to the metal atom "M" have been designated herein as Q and are present in a number such that the compounds described herein are electrically neutral, unless otherwise indicated. In an embodiment, Q comprises an alkyl group, an aryl group or a halide, alternatively Q comprises a halide.

In an embodiment, a catalyst system for the polymerization of olefins comprises a FMC. The FMC may comprise a Cp group, a Fl group, a bridging group and a metal. The Cp group, Fl group, bridging group and metal may be of the type disclosed herein and may form a complex represented by the general chemical formula (III).

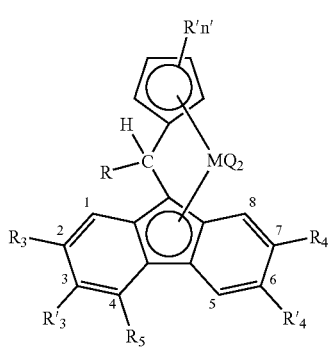

(III)

In formula III, R' may comprise a $C_1$-$C_4$ alkyl group, an aryl group, or combinations thereof and n' may range from 1 to 4. M may be titanium, zirconium or hafnium. In an embodiment, Q may be a halogen, alkyl group, aryl group or combination thereof and $R_3$ and $R_4$ may be the same or different and each may be hydrogen, a methyl group, an isopropyl group, a tertiary butyl group, a phenyl group, a substituted phenyl group or combinations thereof. $R_5$ may be hydrogen, an alkyl group, an aromatic group or combinations thereof. R represents the remainder of the bridging group and may be an alkyl group, an aryl group, a poly-aryl group or combinations thereof. In an embodiment, R is a poly-aryl group comprising at least two aryl groups, alternatively R is one of the compounds represented by the chemical structures given in Group 1.

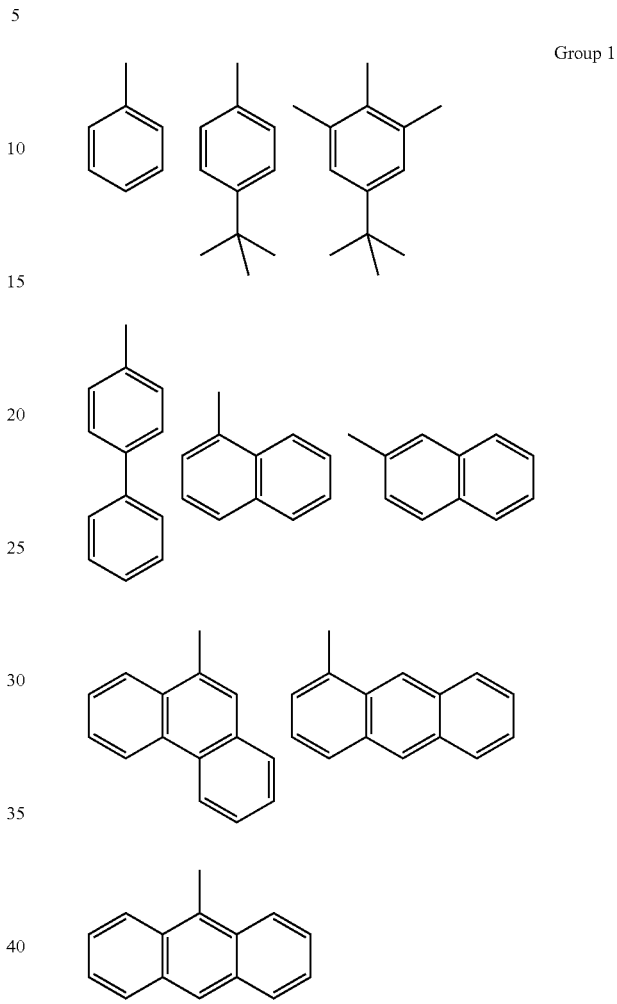

Group 1

In an embodiment a FMC for the polymerization of olefins may be a zirconium metallocene complex represented by the chemical formulas IV-IX given in Table 1 wherein R and R' may be as described for formula III.

TABLE 1

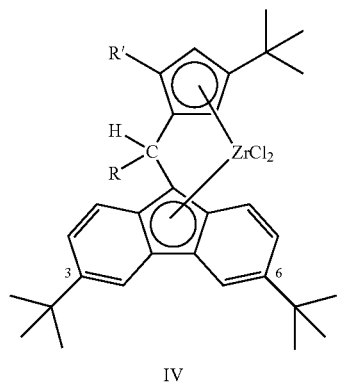

IV

TABLE 1-continued

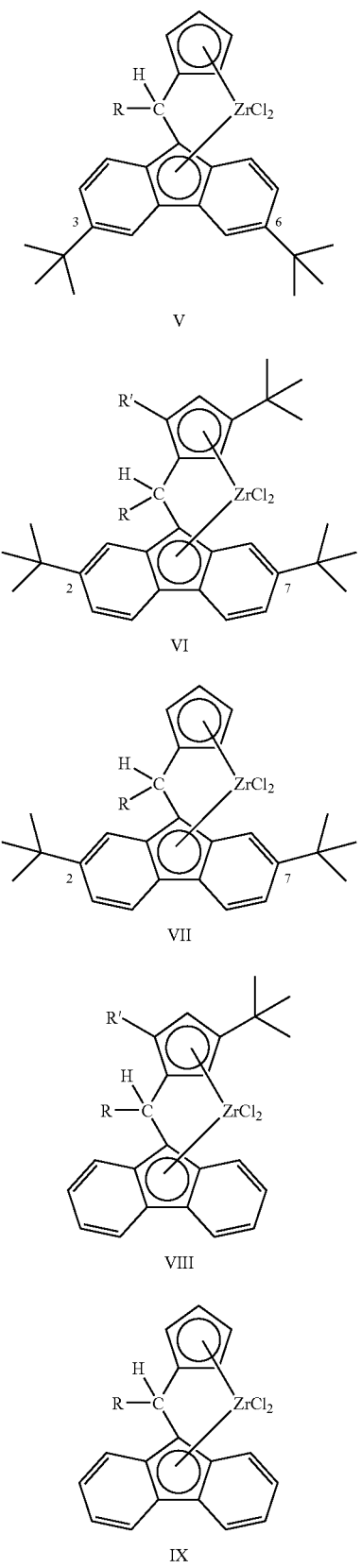

The FMCs of this disclosure may be supported or unsupported. Typical support materials may include talc, inorganic oxides, clays and clay minerals, ion-exchanged layered compounds, diatomaceous earth compounds, zeolites or a resinous support material, such as a polyolefin, for example.

Specific inorganic oxides include without limitation silica, alumina, magnesia, titania and zirconia, for example. The inorganic oxides used as support materials may have an average particle size of from 30 microns to 600 microns or from 30 microns to 100 microns, a surface area of from 50 $m^2$/g to 1,000 $m^2$/g or from 100 $m^2$/g to 400 $m^2$/g and a pore volume of from 0.5 cc/g to 3.5 cc/g or from 0.5 cc/g to 2 cc/g, for example.

Methods for supporting metallocene catalysts are generally known in the art and such methods are disclosed in U.S. Pat. Nos. 5,643,847, 6,143,686, 6,228,795, each of which are incorporated by reference herein.

In an embodiment, the synthesis of catalysts of the type disclosed herein may be carried out by any means known to one of ordinary skill in the art. Alternatively, the catalysts may be synthesized according to a methodology comprising fulvene preparation, bridging ligand preparation and metallation, as shown in Scheme I.

SCHEME I

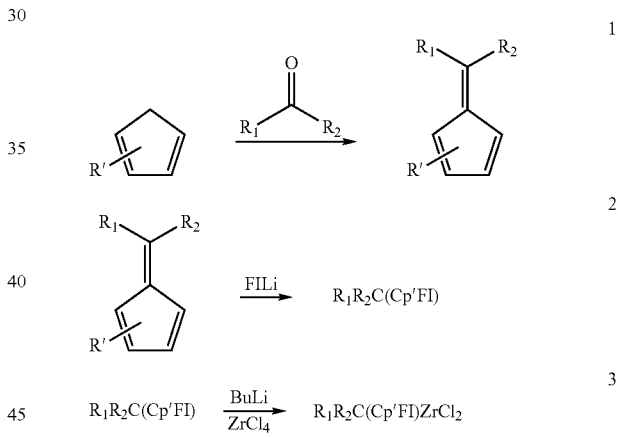

The first step in the scheme involves fulvene synthesis. Fulvene synthesis is a base-catalyzed condensation of cyclopentadienes (or their derivatives) with aldehydes and ketones. The basic condensation agent may be an alkali metalhydrohide, an alkoxide, or an amine, and serves both to form the cylopentadienide ion, which effects nucleophilic attack of the carbonyl atom and to catalyze the dehydration of the intermediate as shown in Scheme II.

SCHEME II

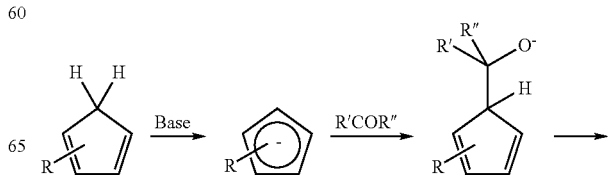

-continued

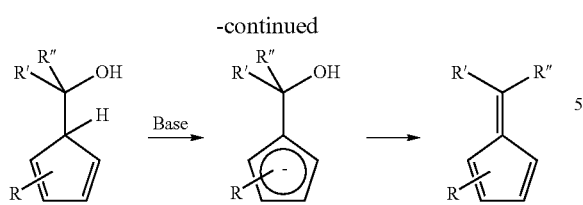

As understood by one of ordinary skill in the art, the yield of fulvene synthesis depends on many factors including the reaction conditions, for example the reaction yield may vary depending on the type and concentration of the base used or on the reaction temperature. Some side reactions can occur during a fulvene formation, which decrease a yield of final product and require additional purification steps. One such side product is fulvene-methanol, the formation of which is depicted in Scheme III:

SCHEME III

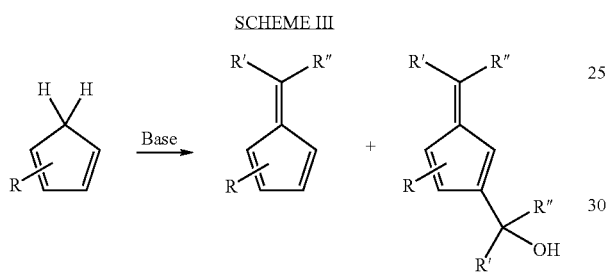

In addition, the cyclopentadienes, and aldehydes/ketones exert steric and electronic effects that are influential on the product yield in fulvene formation reactions. As known to one of ordinary skill in the art, a general rule of nucleophilic addition to carbonyl groups is that electron donating groups, which may be the substituents designated by R' and R" in Scheme III, increase the reaction rate when compared to a reaction carried out with electron withdrawing groups as the substitutents. Without wishing to be limited by theory, the reaction of the base with an aldehyde may proceed faster than the reaction of a base with a ketone based on steric factors. Consequently, bulky substituents on cyclopentadienes (especially, at alpha carbons adjacent to methylene carbons) may dramatically decrease or altogether abolish the ability to form a fulvene, Scheme IV.

SCHEME IV

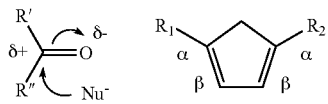

In an embodiment, the catalyst synthesis may begin with the formation of a fulvene such as for example, 6-(1-Naphthyl)-3-tert-butyl-5methyl-fulvene and related fulvenes. One method for the synthesis of a fulvene involves for example the reaction of methyl-tert-butyl-cyclopentadiene with acetone in methanol solution in the presence of pyrrolidine. The reaction may result in 6,6-dimethyl-methyl-butyl-fulvene with 50% yield and take several days for the reaction to occur. This reaction is depicted in Scheme V.

SCHEME V

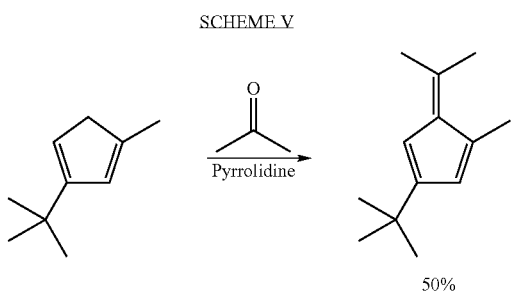

In an embodiment, an aryl substituted fulvene may be prepared by the reaction of a strong base such as sodium methoxide as shown in Scheme VI.

SCHEME VI

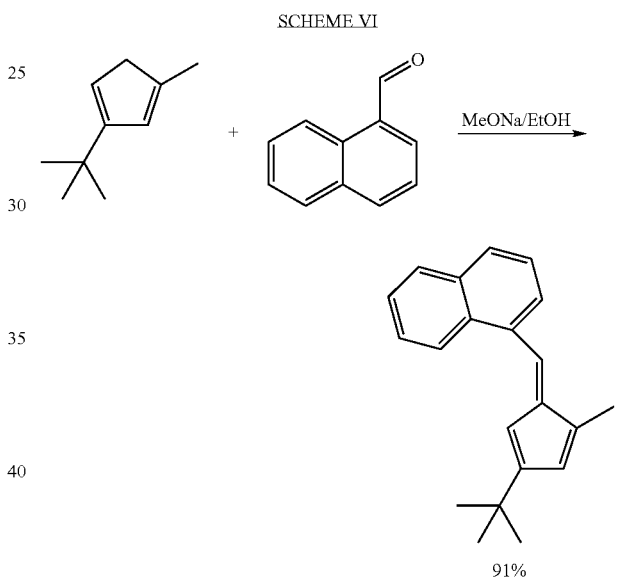

Alternatively, the fulvenes may be produced by a phase transfer reaction (PTR). Such PTRs are known to one of ordinary skill in the art. For example, as shown in Scheme VII the reaction of tert-butyl-cyclopentadiene with acetone in presence of NaOH and Bu$_4$NBr as a PTR catalysts results in the corresponding fulvene with a yield of 95%.

SCHEME VII

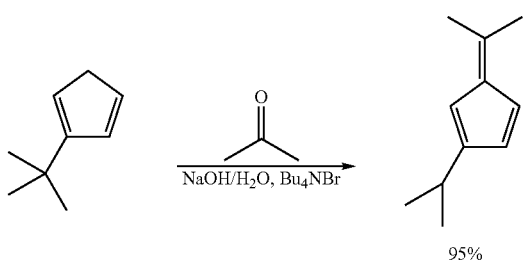

The reaction of methyl-tert-butyl-cyclopentadiene with 1-Naphthaldehyde in presence of NaOH and Bu₄NBr resulted in the corresponding fulvene with 50% yield, Scheme VIII.

SCHEME VIII

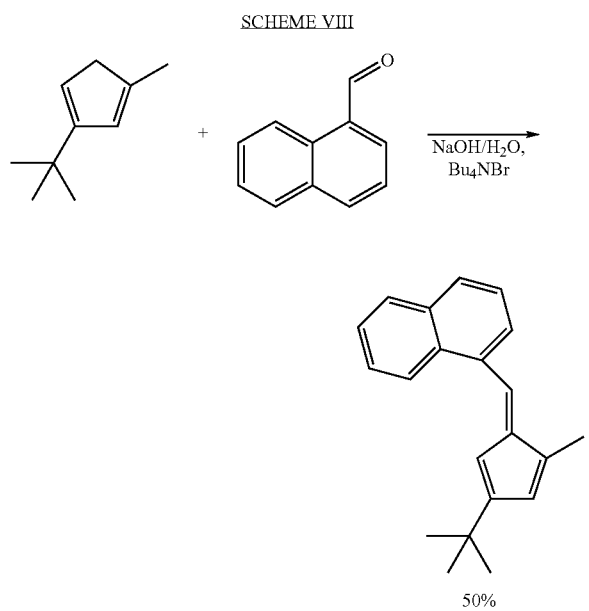

In an embodiment, the fulvene preparation methodologies disclosed herein using sodium methoxide as a base, can be applied for synthesis of different fulvenes. For example, aryl substituted fulvenes (aryl=Phenyl-But, Bi-phenyl), as shown in Scheme IX, may be prepared using this methodology with greater than 80% yield, alternatively greater than 90% yield, alternatively greater than 98% yield.

SCHEME IX

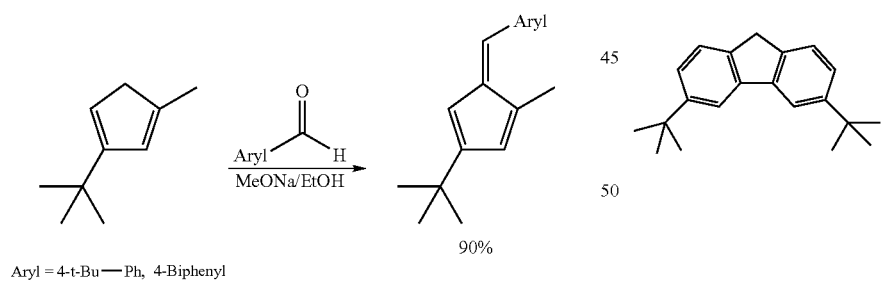

Aryl = 4-t-Bu—Ph, 4-Biphenyl

The process for the preparation of a polymerization catalyst of the type disclosed herein can be exemplified by the preparation of the FMC (1-naphthyl)[(3-Butyl-5-methyl-cyclopentadienyl)(3,6-di-tert-butyl-fluorenyl)]methane zirconium dichloride using the three step process outlined in RXNs 1-3.

In the first reaction, RXN1, preparation of a fulvene was accomplished by the reaction of methyl-tert-butyl-cyclopentadiene with 1-naphthaldehyde in the presence of a base, sodium methoxide.

RXN 1

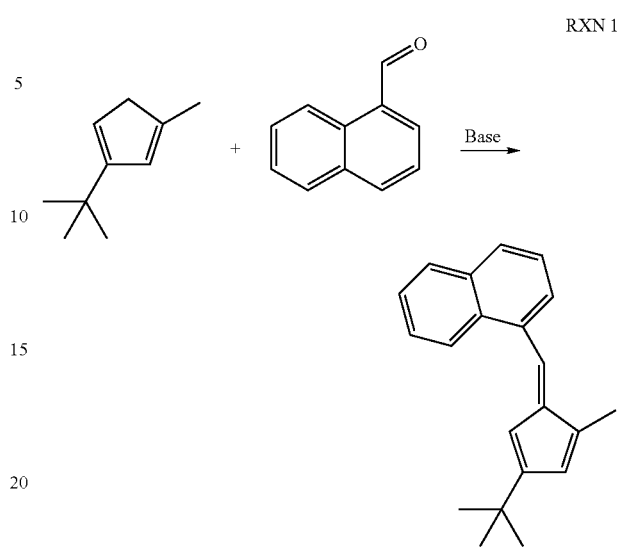

Addition of the bridging ligand was accomplished by reaction of lithium salt of 3,6-di-t-butyl-fluorene with 6-(1-Naphthyl)-3-tert-butyl-5-methyl-fulvene in ether solution, RXN 2. Specifically, treatment of the fluorenyl group with butyllithium results in an intermediate wherein the Li is substituted at position 9 of the fluorenyl group which then reacts further to substitute the fulvene at that position and form the bridged ligand.

RXN2

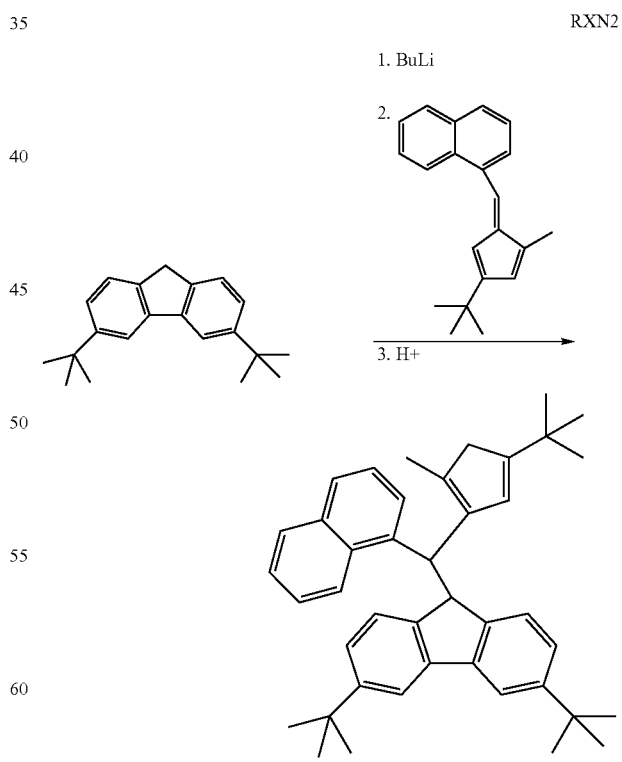

Finally, the complex is metallated, RXN 3, by double deprotonation of the ligand with 2 equiv of n-butyllithium in ether and subsequent reaction of the dilithium salt with ZrCl₄ in toluene affording the FMC, (1-naphthyl)[(3-Butyl-5-methyl-cyclopentadienyl)(3,6-di-tert-butyl-fluorenyl)]methane zirconium dichloride.

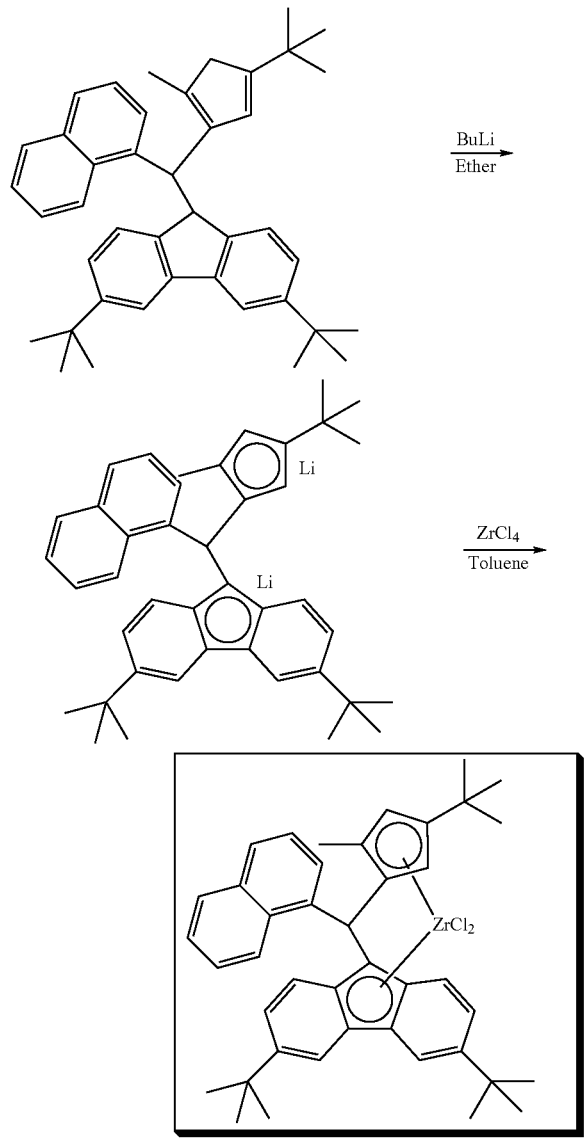

RXN 3

In an embodiment, the preparation of a fulvene as disclosed herein may result in a yield of from 60% to 99%, alternatively of from 70% to 95%, alternatively of from 80% to 95%. In an embodiment, the formation of a bridged Cp and Fl group through the methodology disclosed herein may result in a yield of from 50% to 95%, alternatively of from 60% to 90%, alternatively of from 60% to 95%. In an embodiment, the formation of a FMC of the type disclosed herein through metallation of a bridged Cp, Fl ligand may result in a yield of from 60% to 90%, alternatively of from 50% to 90%, alternatively of from 40% to 90%.

The ligands produced by reactions according to the present disclosure are prepared by means of a very simple and efficient process, which employs inexpensive starting materials and comprises single reaction steps having high yield. Furthermore, this process does not require laborious and time-consuming purification procedures, and thus is particularly suitable to large-scale production.

In an embodiment a catalyst system for the polymerization of olefins comprises a cocatalyst. In employing the catalyst components of the present disclosure (i.e. FMCs) in polymerization procedures, they may be used in conjunction with an activating co-catalyst. Suitable activating co-catalysts may take the form of co-catalysts that are commonly employed in metallocene-catalyzed polymerization reactions. Thus, the activating co-catalyst may take the form of an aluminum co-catalyst such as for example and without limitation alumoxane co-catalysts. Alumoxane co-catalysts are also referred to as aluminoxane or polyhydrocarbyl aluminum oxides. Such compounds include oligomeric or polymeric compounds having repeating units as indicated by the chemical formula shown in the formula X:

(X)

where R is an alkyl group comprising from 1 to 5 carbon atoms. Alumoxanes are well known in the art and are generally prepared by reacting an organo-aluminum compound with water, although other synthetic routes are known to those skilled in the art. Alumoxanes may be either linear polymers or they may be cyclic, as disclosed for example in U.S. Pat. No. 4,404,344. Thus, alumoxane is an oligomeric or polymeric aluminum oxy compound containing chains of alternating aluminum and oxygen atoms whereby the aluminum carries a substituent, such as an alkyl group. The structure of linear and cyclic alumoxanes is generally believed to be represented by the general formula —(Al(R)—O)$_m$— for a cyclic alumoxane, and R$_2$Al—O—(Al(R)—O)$_m$—AlR$_2$ for a linear compound wherein each R may independently comprise a C$_1$-C$_{10}$ hydrocarbyl, alternatively, an alkyl group, a halide or combinations thereof and m is an integer ranging from 1 to 50, alternatively m is 4. Alumoxanes also exist in the configuration of cage or cluster compounds.

Alumoxanes are typically the reaction products of water and an aluminum alkyl, which in addition to an alkyl group may contain halide or alkoxide groups. Reacting several different aluminum alkyl compounds, such as, for example, trimethylaluminum and tri-isobutylaluminum, with water yields so-called modified or mixed alumoxanes. Examples of alumoxanes suitable for use in this disclosure are methylalumoxane and methylalumoxane modified with minor amounts of other higher alkyl groups such as isobutyl. Alumoxanes generally contain minor to substantial amounts of the starting aluminum alkyl compounds. In an embodiment, the co-catalyst comprises poly (methylaluminum oxide), which may be prepared either from trimethylaluminum or tri-isobutylaluminum. Poly (methylaluminum oxide) may also be referred to as poly (isobutylaluminum oxide).

The alkyl alumoxane co-catalyst and transition FMC are employed in any suitable amounts to provide an olefin polymerization catalyst. Suitable aluminum: FMC mole ratios are within the range of 10:1 to 20,000:1 alternatively, within the range of 50:1 to 10,000:1, alternatively, within the range of 100:1 to 5,000:1. Normally, the FMC component and the alumoxane, or other activating co-catalyst as described below, are mixed prior to introduction in the polymerization reactor in a mode of operation such as described in U.S. Pat. No. 4,767,735 which is incorporated by reference herein in its entirety. Other suitable activating co-catalysts which can be used include those catalysts which function to form a catalyst cation with an anion comprising one or more boron atoms. By way of example, the activating co-catalyst may take the form of triphenylcarbenium tetrakis(pentafluorophenyl) boronate as disclosed in U.S. Pat. No. 5,155,080. As described there, the activating co-catalyst produces an anion which functions as a stabilizing anion in a transition metal catalyst system. Suitable noncoordinating anions include $[W(PhF_5)]^-$, $[Mo(PhF_5)]^-$ (wherein $PhF_5$ is pentafluorophenyl), $[ClO_4]^-$, $[S_2O_6]^-$, $[PF_6]^-$, $[SbR_6]^-$ and/or, $[AlR_4]^-$ (wherein each R is independently $C_1$, a $C_1$—$C_5$ alkyl group such as a methyl group, an aryl group, e.g. a phenyl or substituted phenyl group, a fluorinated aryl group or combinations thereof). For a further description of such activating co-catalysts, reference is made to the aforementioned U.S. Pat. No. 5,155,080, the entire disclosure of which was previously incorporated herein. In addition, other activating co-catalysts which are suitable for use in the present disclosure include those catalysts which are supported on fluorinated silica supports. Such catalysts may contain MAO, alternatively such catalysts may not contain MAO.

In addition to the use of an activating co-catalyst, the polymerization reaction may be carried out in the presence of a scavenging agent or polymerization co-catalyst which is added to the polymerization reactor along with the catalyst component and activating co-catalyst. These scavengers can be generally characterized as organometallic compounds of metals of Groups 1A, 2A, and 3B of the Periodic Table of Elements. As a practical matter, organoaluminum compounds are normally used as co-catalysts in polymerization reactions. Specific examples include triethylaluminum, tri-isobutylaluminum, diethylaluminum chloride, diethylaluminum hydride and the like. Scavenging co-catalysts normally employed may include methylalumoxane (MAO), triethylaluminum (TEAL), tri-isobutylaluminum (TIBAL) or combinations thereof.

The activators may or may not be associated with or bound to a support, either in association with the catalyst (e.g, FMC) or separate from the catalyst component, such as described by Gregory G. Hlalky, *Heterogeneous Single-Site Catalysts for Olefin Polymerization* 100(4) CHEMICAL REVIEWS 1347-1374 (2000).

As indicated elsewhere herein, catalyst systems comprising an FMC of the type disclosed herein may be used to catalyze the polymerization of alpha olefins. Once the catalyst system is prepared, as described above and/or as known to one skilled in the art, a variety of processes may be carried out using the catalyst system. The equipment, process conditions, reactants, additives and other materials used in polymerization processes will vary in a given process, depending on the desired composition and properties of the polymer being formed.

In certain embodiments, the processes described above generally include polymerizing olefin monomers. The olefin monomers may include $C_2$ to $C_{30}$ olefin monomers, or $C_2$ to $C_{12}$ olefin monomers (e.g., ethylene, propylene, butene, pentene, methylpentene, hexene, octene and decene), for example. Other monomers include ethylenically unsaturated monomers, $C_4$ to $C_{18}$ diolefins, conjugated or nonconjugated dienes, polyenes, vinyl monomers and cyclic olefins, for example. Non-limiting examples of other monomers may include norbornene, nobornadiene, isobutylene, isoprene, vinylbenzocyclobutane, sytrene, alkyl substituted styrene, ethylidene norbornene, dicyclopentadiene and cyclopentene, for example. The formed polymer may include homopolymers, copolymers or terpolymers, for example.

The olefin polymerization may be carried out using solution phase, gas phase, slurry phase, bulk phase, high pressure processes or combinations thereof, for example. See, for example, U.S. Pat. Nos. 5,525,678, 6,420,580, 6,380,328, 6,359,072, 6,346,586, 6,340,730, 6,339,134, 6,300,436, 6,274,684, 6,271,323, 6,248,845, 6,245,868, 6,245,705, 6,242,545, 6,211,105, 6,207,606, 6,180,735 and 6,147,173, which are incorporated by reference herein.

Examples of solution processes are described in U.S. Pat. Nos. 4,271,060, 5,001,205, 5,236,998 and 5,589,555, which are incorporated by reference herein.

One example of a gas phase polymerization process includes a continuous cycle system, wherein a cycling gas stream (otherwise known as a recycle stream or fluidizing medium) is heated in a reactor by heat of polymerization. The heat is removed from the cycling gas stream in another part of the cycle by a cooling system external to the reactor. The cycling gas stream containing one or more monomers may be continuously cycled through a fluidized bed in the presence of a catalyst under reactive conditions. The cycling gas stream is generally withdrawn from the fluidized bed and recycled back into the reactor. Simultaneously, polymer product may be withdrawn from the reactor and fresh monomer may be added to replace the polymerized monomer. The reactor pressure in a gas phase process may vary from 100 psig to 500 psig, or from 200 psig to 400 psig or from 250 psig to 350 psig, for example. The reactor temperature in a gas phase process may vary from 30° C. to 120° C., or from 60° C. to 115° C., or from 70° C. to 110° C. or from 70° C. to 95° C., for example. See, for example, U.S. Pat. Nos. 4,543,399, 4,588,790, 5,028,670, 5,317,036, 5,352,749, 5,405,922, 5,436,304, 5,456,471, 5,462,999, 5,616,661, 5,627,242, 5,665,818, 5,677,375 and 5,668,228, which are incorporated by reference herein.

Slurry phase processes generally include forming a suspension of solid, particulate polymer in a liquid polymerization medium, to which monomers and optionally hydrogen, along with catalyst, are added. The suspension (which may include diluents) may be intermittently or continuously removed from the reactor where the volatile components can be separated from the polymer and recycled, optionally after a distillation, to the reactor. The liquefied diluent employed in the polymerization medium may include a $C_3$ to $C_7$ alkane (e.g., hexane or isobutene), for example. The medium employed is generally liquid under the conditions of polymerization and relatively inert. A bulk phase process is similar to that of a slurry process. However, a process may be a bulk process, a slurry process or a bulk slurry process, for example.

As stated previously, hydrogen may be added to the process for a variety of reasons. For example, hydrogen may be added to increase the melt flow of the resultant polymer, to increase the catalyst activity or, for molecular weight control of the resultant polymer. In an embodiment, hydrogen may be present in the reaction mixture in an amount of from 0 to 400 ppm, alternatively from 5 ppm to 200 ppm, alternatively from 10 ppm to 150 ppm.

In an embodiment, the polymerization carried out is a copolymerization of alpha-olefin monomers. Alternatively, the polymerization process is copolymerization of ethylene with a second alpha-olefin monomer. In such embodiments, ethylene may be present in the feed in an amount of from 0 to 90 wt. %, alternatively from 0.5 wt. % to 50 wt. %, alternatively from 0.5 wt. % to 10 wt. %.

In a specific embodiment, a slurry process or a bulk process may be carried out continuously in one or more loop reactors. The catalyst, as slurry or as a dry free flowing powder, may be injected regularly to the reactor loop, which can itself be filled with circulating slurry of growing polymer particles in a diluent, for example. The loop reactor may be maintained at a pressure of from 27 bar to 45 bar and a temperature of from 38° C. to 121° C., for example. Reaction heat may be removed through the loop wall via any method known to one skilled in the art, such as via a double-jacketed pipe.

Alternatively, other types of polymerization processes may be used, such stirred reactors in series, parallel or combinations thereof, for example. Upon removal from the reactor, the polymer may be passed to a polymer recovery system for further processing, such as addition of additives and/or extrusion, for example.

In an embodiment, the FMCs and catalyst systems comprising the FMCs disclosed are employed in the production of stereoregular polymeric compositions having a desired combination of physical properties such as molecular weight, melting temperature and tacticity. In an embodiment, the FMCs and catalyst systems comprising an FMC of this disclosure are used in the production of copolymers of propylene with another alpha-olefin. Alternatively the catalysts and catalyst systems of this disclosure are used in the production of isotactic propylene. In an embodiment, the isotactic polypropylene may have a molecular weight of less than 100,000 Daltons, alternatively from 100,000 to 1,000,000 Daltons, alternatively of from 200,000 to 800,000 Daltons. In an embodiment the isotactic polypropylene may have a melting temperature of from 120° C. to 161° C., alternatively from 120° C. to 145° C., alternatively from 159° C. to 161° C. The isotactic polypropylene produced by the catalyst of this disclosure may be further characterized by a high tacticity ranging from 97% to 0.99% mmmm, alternatively from 96% to 99%, alternatively from 95% to 99%. In an embodiment, the catalysts and catalyst systems of this disclosure are used in the production of copolymers of ethylene with another alpha-olefin monomer such as for example propylene. In such embodiments, the percentage ethylene in the copolymer product may range from 0 to 80 wt. %, alternatively from 0.5 wt. % to 50 wt. %, alternatively from 0.5 wt. % to 30 wt. %.

The polymeric compositions produced using the catalysts or catalyst systems of this disclosure may be useful in applications known to one skilled in the art, such as forming operations (e.g., film, sheet, pipe and fiber extrusion and co-extrusion as well as blow molding, injection molding and rotary molding). Films include blown or cast films formed by co-extrusion or by lamination useful as shrink film, cling film, stretch film, sealing films, oriented films, snack packaging, heavy duty bags, grocery sacks, baked and frozen food packaging, medical packaging, industrial liners, and membranes, for example, in food-contact and non-food contact application. Fibers include melt spinning, solution spinning and melt blown fiber operations for use in woven or non-woven form to make filters, diaper fabrics, medical garments and geotextiles, for example. Extruded articles include medical tubing, wire and cable coatings, geomembranes and pond liners, for example. Molded articles include single and multi-layered constructions in the form of bottles, tanks, large hollow articles, rigid food containers and toys, for example.

Catalyst systems comprising the FMCs of this disclosure may produce isotactic polypropylene with a desirable combination of physical properties. In one embodiment, the isotactic polypropylene may be characterized by a molecular weight of from 400,000 to 1,000,000 Daltons, a melting temperature of from 159° C. to 161° C. and a tacticity of from 97% to 99% mmmm. Catalysts useful for the production of isotactic polypropylene of this type may be characterized by the general formula XI:

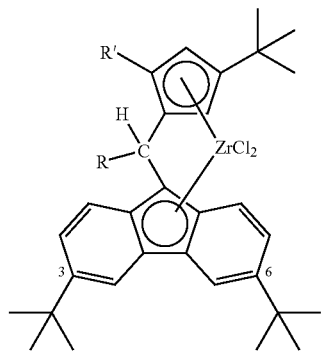

(XI)

where R' comprises H or Me and R comprises Me or a compound selected from the following group:

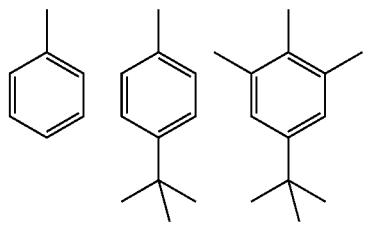

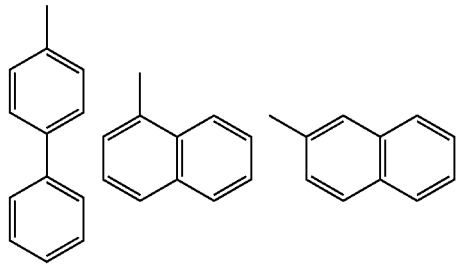

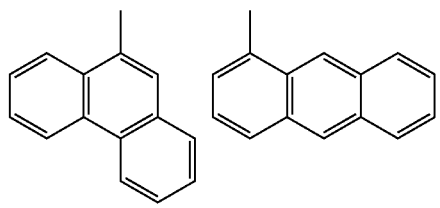

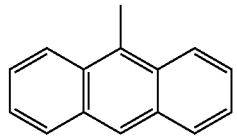

In an alternative embodiment, the isotactic polypropylene produced using the catalyst systems comprising the FMCs of this disclosure may be characterized by a molecular weight of from 100,000 to 1,000,000 Daltons and a melting temperature of from 120° C. to 145° C. Catalysts useful for the production of isotactic polypropylene of this type may be characterized by the general formula XII:

(XII)

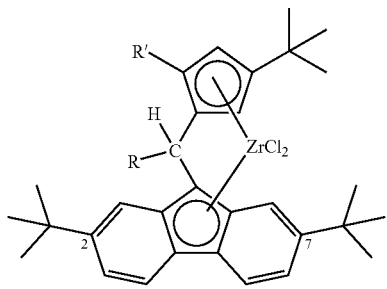

where R' comprises H or Me and R comprises Me or a compound selected from the following group:

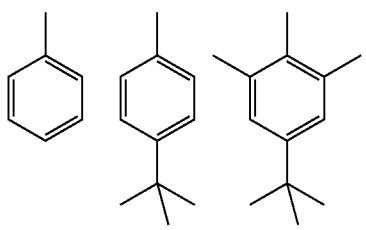

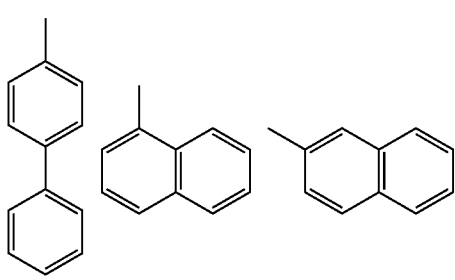

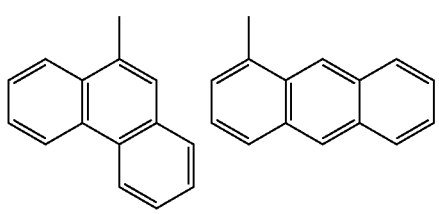

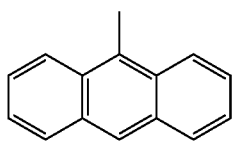

Alternatively, the isotactic polypropylene produced using the catalyst systems comprising the FMCs of this disclosure may be characterized by a molecular weight of less than 100,000 Daltons and a melting temperature of from 120° C. to 145° C. Catalysts useful for the production of isotactic polypropylene of this type may be characterized by the general formula XIII:

(XIII)

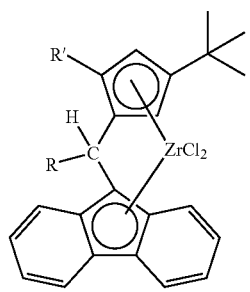

where R' comprises H or Me and R comprises Me or a compound selected from the following group:

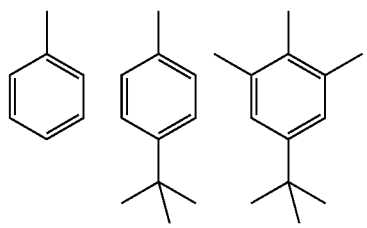

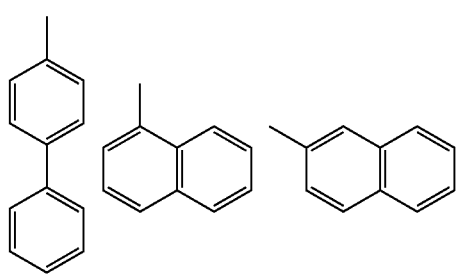

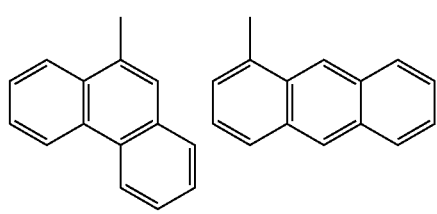

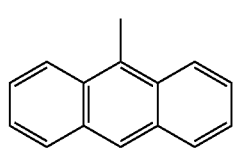

The catalysts of the present disclosure can be advantageously used in propylene polymerization to produce isotactic polypropylenes having a desired combination of physical properties. Desired features of the catalysts of the present disclosure are due to a unique combination of structural parameters of the catalysts and substitutions of the cyclopentadienyl and fluorenyl rings. In addition, the catalysts of the present disclosure can be used in copolymerization of propylene with olefins, e.g. ethylene to yield random or impact copolymers with low melt flow rates.

EXAMPLES

Example 1

The catalyst, (1-Naphthyl)-[(5-methyl-3-tert-butyl)3,6-di-tert-butyl-(fluorenyl)] methane zirconium dichloride, hereafter referred to as Catalyst A, was synthesized. The synthesis began with preparation of a fulvene, 6-(1-Naphthyl)-5-methyl-3-tert-butyl-fulvene as follows: to a solution of methyl-tert-butylcyclopentadiene (4.35 g, 32.0 mmol) and 1-naphthaldehyde (5.0 g, 32.0 mmol)) in absolute ethanol (50 ml) was added a small portion of sodium methoxide (4.5 g) under stirring and the mixture was stirred for 1 h. The reaction was quenched with water and extracted with ether. The solvents were evaporated under vacuum to give an orange liquid, which was purified by column chromatography (silica gel, hexane/$CH_2Cl_2$=8/1) (Yield 4.4 g). The chemical shifts from the $^1$H NMR in deuterated chloroform ($CDCl_3$) are as follows: δ 8.1, 7.9, and 7.6 (m, Naphth), 7.70 (s, $^1$H, H-6), 6.36 and 6.02 (br S, $^2$H, H-Cp), 2.31 (s, $^3$H, Me), 1.23 (s, 9H, t-Bu).

The synthesis continued with the addition of the fulvene to a substituted fluorenyl ligand to produce (1-Naphthyl)-[(5-methyl-3-tert-butyl)3,6-di-tert-butyl-(fluorenyl)]methane. Butyllithium (3.0 ml, 1.6M in hexane, 4.8 mmol) was added to 3,6-di-t-butyl-fluorene (1.29 g, 4.67 mmol) in ether (20 ml) at −78° C. The reaction mixture was allowed to warm to room temperature and stirred for 4 h. 6-(1-Naphthyl)-5-methyl-3-tert-butyl-fulvene (1.3 g, 4.74 mmol) in ether (5 ml) was added to the reaction mixture at −40° C. The reaction was stirred at room temperature for 1.5 h. The reaction mixture was quenched with water, extracted with ether, dried over $MgSO_4$, and evaporated under vacuum to afford the desired ligand.

Metallation of the bridged cyclopentadienyl fluorenyl ligand was carried out. Butyllithium (2.5 ml, 1.6M, 4.0 mmol) was added to (1-naphthyl)-[(5-methyl-3-tert-butyl)3,6-di-tert-butyl-(fluorenyl)]methane (1.05 g, 1.91 mmol) in ether (20 ml) at −78° C. The reaction mixture was allowed to heat to room temperature and the reaction was continued for 2.5 h. The solvent was removed under vacuum. $ZrCl_4$ (440 mg, 1.89 mmol) was added to the reaction mixture. Toluene (15 ml) was added at −40° C. and the reaction was stirred at room temperature for 2 days. The solvent was removed under vacuum to produce (1-Naphthyl)-[(5-methyl-3-tert-butyl)3,6-di-tert-butyl-(fluorenyl)]methane zirconium dichloride.

The catalyst (2-Naphthyl)-[(5-methyl-3-tert-butyl)-3,6-di-tert-butyl (fluorenyl)] methane zirconium dichloride, hereafter referred to as Catalyst B, was synthesized as follows: to a solution of methyl-tert-butylcyclopentadiene (4.38 g, 32.2 mmol) and 2-naphthaldehyde (5.0 g, 32.0 mmol) in absolute ethanol (75 ml) was added a small portion of sodium methoxide (4.5 g) under stirring and the mixture was stirred for 1 h. The reaction was quenched with water and extracted with ether. The solvents were evaporated under vacuum to give an orange solid, which was purified by column chromatography (silica gel, hexane/$CH_2Cl_2$=8/1). The $^1$H NMR was run in $CDCl_3$ and the chemical shifts are as follows: δ 7.98, 7.95 (s, 1H, Naph), 7.15 and 7.13 (s, 1H, Naph), 7.8, 7.7 and 7.5 (m, Naph+H), 6.22 and 6.21 (br s, 2H, H-Cp), 2.18 and 2.15 (s, 3H, Me), 1.20 and 1.17 (s, 9H, t-Bu). The synthesis proceeded with the formation of the bridged Fl-Cp ligand: (2-Naphthyl)-[(5-methyl-3-tert-butyl)3,6-di-tert-butyl-(fluorenyl)]methane. Butyllithium (2.8 ml, 1.6M in hexane, 4.48 mmol) was added to 3,6-di-t-butyl-fluorene (1.20 g, 4.35 mmol) in ether (20 ml) at −78° C. The reaction mixture was allowed to warm to room temperature and stirred for 4 h. 6-(2-Naphthyl)-5-methyl-3-tert-butyl-fulvene (1.19 g, 4.34 mmol) in ether (10 ml) was added to the reaction mixture at −40° C. The reaction was stirred at room temperature for 1.5 h. The reaction mixture was quenched with water, extracted with ether, dried over $MgSO_4$, and evaporated under vacuum to afford the desired ligand. The ligand was purified by column chromatography (silica gel, hexane/$CH_2Cl_2$=7/1) and washed with hot ethanol.

The metallated catalyst (2-Naphthyl)-[(5-methyl-3-tert-butyl)3,6-di-tert-butyl-(fluorenyl)]methane zirconium dichloride was prepared. Butyllithium (2.5 ml, 1.6M, 4.0 mmol) was added to (2-naphthyl)-[(5-methyl-3-tert-butyl)3,6-di-tert-butyl-(fluorenyl)]methane (1.06 g, 1.93 mmol) in ether (20 ml) at −78° C. The reaction mixture was allowed to heat to room temperature and the reaction was continued for 3 h. The solvent was removed under vacuum. $ZrCl_4$ (460 mg, 1.97 mmol) was added to the reaction mixture. Toluene (15 ml) was added at −40° C. and the reaction was stirred at room temperature overnight. Herein, overnight refers to time period equal to or greater than 8 hours. The solvent was removed under vacuum.

Example 2

Catalysts A and B as synthesized according to the conditions given in Example 1 are characterized by having a naphthyl group as the bridging ligand, a symmetric 3,6 tert-butyl substitution of the fluorenyl group and a 5-methyl, 3-tert-butyl substitution of the cyclopentadienyl group. The general formulas of these catalysts are given below in Structures XIV and XV for Catalysts A and B repsectively.

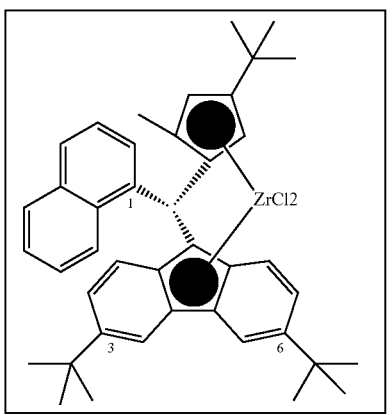

Structure XIV

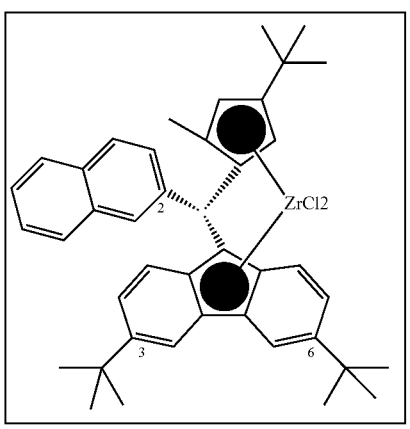

Structure XV

The polymerization activities of these FMCs are compared to that of Catalyst C, Structure XVI, which has a dimethyl bridging group and an unsubstituted fluorenyl group.

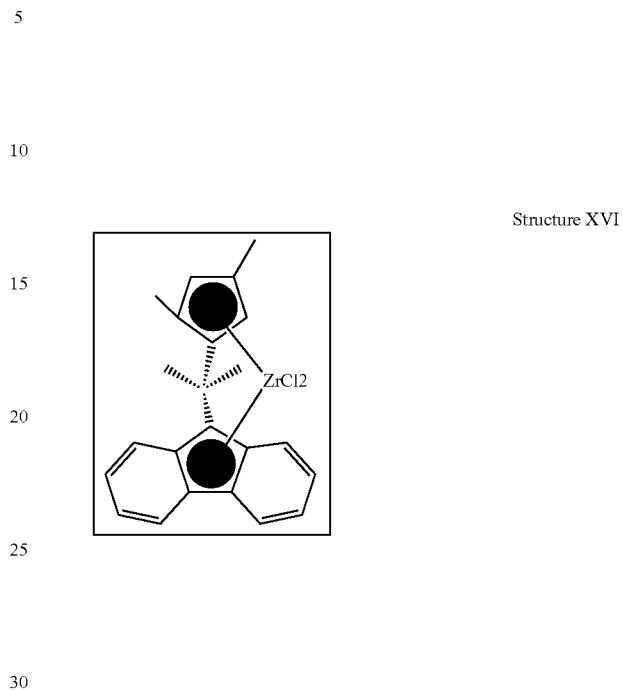

Structure XVI

Homogeneous polymerization was conducted in bulk propylene in a 10× Multi-Clave reactor at 20 and 60° C. using Catalysts A-C without purification. The reactions were run for 30 minutes in the absence of hydrogen with a FMC/MAO of 1/1000. The results in terms of polymerization parameters and polymer properties are given in Table 2. Catalyst A produced polymers with melting points of 161 and 159° C. at polymerization temperatures of 20 and 60° C. respectively.

TABLE 2

| # | Catalyst (mg) | Temp °C. | Polymer, g | Activity, g/g/h | Tm, °C. | Tc °C. | Mw/1000 | Mw/Mn | Mz/Mw |
|---|---|---|---|---|---|---|---|---|---|
| 1 | A (1.0 mg) | 20 | 0.5 | 1,000 | 161.0 | 118.5 | 322.0 | 3.7 | 2.1 |
| 2 | A (0.3 mg) | 60 | n.d. | — | 158.7 | 118.3 | 665.0 | 5.3 | 3.4 |
| 3 | B (0.25 mg) | 60 | 0.3 | 2,400 | 161.0 | 122.8 | 634.0 | 4.2 | 2.8 |
| 4 | C (0.1 mg) (comparison) | 60 | nd | — | 148 | 104.6 | 370.1 | 5.1 | 1.7 |

The results demonstrate that the new catalysts, Catalysts A and B, produced polymers with melting temperature 13° higher than that produced by Catalyst C. The polymerization with Catalyst B at 60° C. resulted in a polymer with 161° C. melting temperature. Both catalysts A and B produced polymers with a molecular weight of between 665,000-634,000. A broader molecular weight distribution was also observed due to the presence of a low molecular fraction.

Example 3

The effect of a silica support on the polymerization activity of the novel catalysts was determined. Specifically, Catalyst A and B were supported on silica supports available from Asahi Glass Co., Ltd. under the designation G-952. G-952 silica with 2 wt % loading of the Catalyst A or Catalyst B were tested in a 6-parallel reactor set. The reactions were carried out at 60° C. for 30 min in the presence or absence of $H_2$ as indicated in Table 3 which also presents the results in terms of polymerization parameters and polymer. For comparison, Catalyst C was also supported with G-952 silica and tested under the same conditions.

TABLE 3

| # | Catalyst (mg) | $H_2$, ppm | Polymer, g | Activity, g/g/cat/h | Tm, °C. | Tc, °C. | Mw/1000 | Mw/Mn | Mz/Mw |
|---|---|---|---|---|---|---|---|---|---|
| 5 | A/G-952 (10 mg) | 20 | 6.5 | 1,300 | 157.7 | 112.3 | 288 | 3.4 | 2.6 |
| 6 | A/G-952 (10 mg) | 60 | 10 | 2,000 | 157.9 | 112.8 | 194 | 3.2 | 2.5 |
| 7 | B/G-952 (10 mg) | 0 | trace | — | 139.2 | 101.1 | 393 | 3.9 | 2.4 |
| 8 | B/G-952 (10 mg) | 20 | 4 | 800 | 157.7 | 111.5 | 247 | 2.8 | 2.5 |
| 9* | B/G-952 (5 mg) | 60 | — | — | 157.4 | 112.5 | 201 | 2.7 | 2.4 |
| 10 | B/G-952 (10 mg) | 60 | 6 | 1,200 | 157.9 | 111.5 | 182 | 2.7 | 2.4 |
| 11 | C/G-952 (5 mg) Comparison | 0 | — | — | 140.4 | 105.5 | 492 | 3.1 | 2.5 |
| 12 | C/G952 (10 mg) Comparison | 60 | 26 | 5,200 | 145.7 | 105.3 | 149 | 2.7 | 2.3 |

*= Reaction carried out at 67° C.

The results demonstrate that both the novel Catalysts A and B exhibit less activity than the comparative catalyst, Catalyst C. Catalyst A is more active than the 2-substituted analog, Catalyst B. The new catalysts A and B produced polymers with a melting temperature of 158° C. that is 12° higher than for Catalyst C. The molecular weight of polymers, produced by Catalysts A and B depend on the hydrogen concentration and is in a range of 400,000 for polymerization without $H_2$, 290,000-250,000 at 20 ppm of $H_2$ and 200,000 at 60 ppm of $H_2$. The tacticity of the polypropylene samples produced were determined and are compared in Table 4.

TABLE 4

| | Catalyst | | | | | | |
|---|---|---|---|---|---|---|---|
| # | Catalyst A/G-952 5 | Catalyst A/G-952 6 | Catalyst B/G-952 7 | Catalyst /G-952 8 | Catalyst B/G-952 9 | Catalyst C/G-952 Comparison 11 | Catalyst C/G-952 Comparison 12 |
| $H_2$, ppm | 20 | 60 | 0 | 20 | 60 | 0 | 60 |
| (%) mmmm | 95.9 | 95.1 | 94.8 | 97.3 | 97.4 | 88.6 | 90.5 |
| mmmr | 1.6 | 1.7 | 2.3 | 1.1 | 1.0 | 4.3 | 3.6 |
| rmmr | 0.1 | 0.2 | 0.3 | 0.0 | 0.0 | 0.2 | 0.0 |
| mmrr | 1.2 | 1.3 | 1.7 | 0.8 | 0.8 | 3.9 | 3.5 |
| xmrx | 0.2 | 0.4 | 0.0 | 0.2 | 0.2 | 0.5 | 0.5 |
| mmrr | 0.0 | 0.0 | 0.0 | 0.0 | 0.0 | 0.0 | 0.0 |
| rrrr | 0.3 | 0.5 | 0.0 | 0.0 | 0.0 | 0.1 | 0.1 |
| rrrm | 0.3 | 0.4 | 0.3 | 0.2 | 0.1 | 0.3 | 0.2 |
| mrrm | 0.5 | 0.5 | 0.5 | 0.4 | 0.4 | 2.0 | 1.6 |
| % meso | 98.3 | 97.8 | 98.3 | 98.9 | 99.0 | 95.4 | 96.1 |
| % racemic | 1.7 | 2.2 | 1.7 | 1.1 | 1.0 | 4.6 | 3.9 |
| % error | 0.2 | 0.4 | 0.3 | 0.1 | 0.1 | 0.5 | 0.2 |
| def/1000 C. | 1.2 | 1.9 | 1.7 | 0.6 | 0.5 | 2.3 | 1.2 |

The results demonstrate a higher percentage of meso pentads (% mmmmm) is formed with Catalysts A and B than seen with the comparative catalyst, Catalyst C.

Example 4

An ethylene/propylene copolymerization with Catalyst A supported on G-952 silica was conducted at 60° C. in 2 L bench reactor and 6x-parallel reactors under different initial hydrogen and ethylene concentrations. The results are summarized in Tables 5 and 6.

TABLE 5

| # | $C_2$, wt %, in feed | Polymer, g | Activity, g/g/cat/h | Tm, °C. | Delta H, J/g | $C_2$, wt % in copo | MF | Mw/1000 | Mw/Mn | Mz/Mw | %, XS |
|---|---|---|---|---|---|---|---|---|---|---|---|
| 13 | 0   | 36 | 1,800 | 157.0 | 91 | 0   | 42   | 153.4 | 3.7 | 2.1 | 2.26 |
| 14 | 0.5 | 30 | 1,500 | 141.4 | 76 | 2.4 | 310  | 82.2  | 2.7 | 1.9 | 5.94 |
| 15 | 1.5 | 48 | 2,400 | 121.0 | 38 | 5.7 | 1000 | 67.2  | 2.4 | 1.7 | 9.69 |

TABLE 6

| # | $H_2$, ppm | $C_2$, wt %, in feed | Polymer, g | Activity, g/g/cat/h | Tm, °C. | $C_2$, wt % in copo | MF | Mw/1000 | Mw/Mn | Mz/Mw | %, XS |
|---|---|---|---|---|---|---|---|---|---|---|---|
| 16 | 20 | 0   | 6.5 | 1,300 | 157.7 | 0   | —    | 288   | 3.4 | 2.6 | —    |
| 17 | 20 | 0.5 | 7.4 | 592   | 144   | 1.6 | 70   | 140.1 | 2.9 | 2.0 | 5.4  |
| 18 | 20 | 1.0 | 10  | 800   | 133.7 | 4.9 | 180  | 100.4 | 2.4 | 1.8 | 8.40 |
| 19[a] | 60 | 0   | 11  | 1,100 | 155.0 | 0   | 11.4 | 237.0 | 3.7 | 2.1 | —    |
| 20[a] | 0  | 1.0 | —   | —     | 130.4 | 3.6 | —    | 127.3 | 3.1 | 2.0 | —    |

[a] = reactions run at 70° C.,
copo = copolymer

Figure 2:
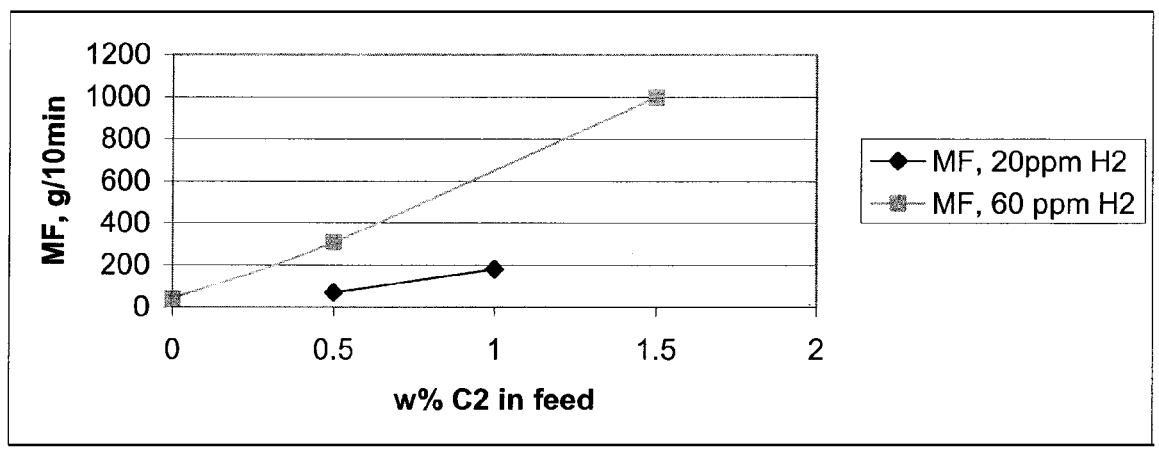
FIG. 2 is a plot of percent ethylene in the feed versus melt flow temperatures for polymers produced using Catalyst A.

The catalyst activity increases with increasing ethylene concentration in feed under hydrogen concentration, FIG. 1. The activity of 2,400 g/gCat/h was observed under the initial hydrogen concentration of 60 ppm and ethylene concentration 1.5 wt %. The melt flow dramatically increased with increasing ethylene content under the same initial hydrogen concentration, FIG. 2. Catalyst A produced a copolymer with melt flow of 180 g/10 min with ethylene contents of 4.9 wt % and melting point of 121° C. under polymerization with 20 ppm of hydrogen. The ultra melt flow resins (MF=1000 g/10 min) were obtained under hydrogen concentration of 60 ppm. The tacticity of the copolymers produced in Samples 2 and 3 was also determined and the results are given in Table 7.

TABLE 7

| | # | |
|---|---|---|
| | 17 | 18 |
| mole % E  | 3.5  | 8.3  |
| mole % P  | 96.5 | 91.7 |
| wt % E    | 2.4  | 5.7  |
| wt % P    | 97.6 | 94.3 |
| mole % PP | 93.6 | 85.1 |

TABLE 7-continued

| | # | |
|---|---|---|
| | 17 | 18 |
| mole % PE  | 5.8  | 13.3 |
| mole % EE  | 0.4  | 1.0  |
| mole % PPP | 84.9 | 73.9 |
| mole % PPE | 7.4  | 12.1 |
| mole % EPE | 4.2  | 5.8  |
| mole % PEP | 2.8  | 6.3  |
| mole % PEE | 0.4  | 1.6  |
| mole % EEE | 0.3  | 0.2  |

The $^{13}$C NMR indicates that copolymer produced by Catalyst A is dramatically enriched in ethylene compared to the feed composition. The EPE triad is more enriched than would be predicted from truly random copolymerization, therefore, Catalyst A has a tendency towards alternating copolymerization between ethylene and propylene.

The results of Examples 2-4 demonstrate that the novel catalysts exemplified by Catalysts A and B are useful in the production of isotactic polypropylene with a high molecular weight, high melting temperature and high tacticity.

Example 5

A catalyst containing a methyl group as the bridging ligand, Catalyst D, was prepared and used in the polymerization of propylene. The catalyst structure is depicted in Structure XVII. The polymerization of propylene was carried out as described in Example 2 and the results of the polymerization are presented in Table 8.

Structure XVII

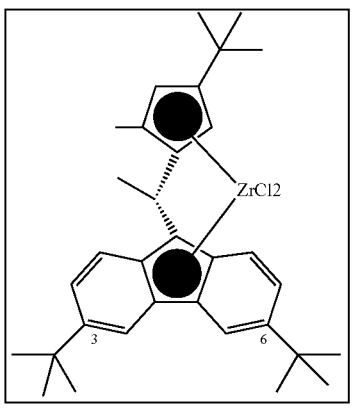

Catalyst E was synthesized using the general methodology described in Example 1. Specifically, synthesis of 6-(4-t-Butyl-phenyl)-5-methyl-3-tert-butyl-fulvene) was carried out as follows: to a solution of methyl-tert-butylcyclopentadiene (4.42 g, 32.5 mmol) and 4-t-butyl-benzaldehyde (5.15 g, 31.8 mmol) in absolute ethanol (50 ml) was added a small portion of sodium methoxide (4.5 g) under stirring and the mixture was stirred for 2 h. The reaction was quenched with water and extracted with ether. The solvents were evaporated under vacuum to give an orange liquid, which was purified by column chromatography (silica gel, hexane/$CH_2Cl_2$=8/1). The reaction resulted in 8.0 g of fulvene or a yield of 90%. The $^1H$ NMR was carried out and the chemical shifts are as follows: δ 7.55 and 7.46 each (d, J=4 Hz, 2H, Ph), 7.03 (s, 1H, H-bridge), 6.27 and 6.22 (br s, 2H, Cp), 6.29 and 6.26 (br s, Cp-isomers), 2.18 (s, 3H, Me), 1.39 (s, 9H, t-Bu (Ph)), 1.23 (s, 9H, t-Bu (Cp)).

TABLE 8

| # | Catalyst (mg) | Polymer, g | Activity, g/g/cat/h | Tmelt, °C. | Tcryst, °C. | Mw/1000 | Mw/Mn | Mz/Mw |
|---|---|---|---|---|---|---|---|---|
| 21[a] | D (0.12) | 0.4 | 6,700 | 154.0 | 113.3 | 507.8 | 5.0 | 2.1 |

[a]13 min to set up 50° C., the reaction temperature 50-60° C.

The activity of Catalyst D is considerably higher than that observed with the Catalysts A or B (see Table 3) and is similar to that observed with the Catalyst C used for comparison. Furthermore, polypropylene resins produced using Catalyst D exhibit a moderate melting temperature, 154.0° C., with a moderate average molecular weight of 507,800 Daltons.

Example 6

A catalyst containing a mono-phenyl tert-butyl group as the bridging ligand was prepared, Catalyst E. The structure of the catalyst employed is shown as Structure XVIII.

Structure XVIII

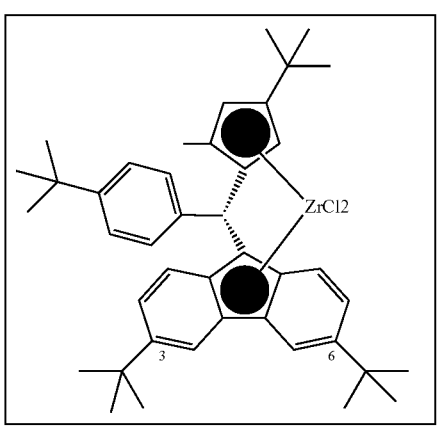

The synthesis of (4-t-Butyl-phenyl)-[(5-methyl-3-tert-butyl)3,6-di-tert-butyl-(fluorenyl)]methane was carried out as follows: Butyllithium (2.4 ml, 1.6M in hexane, 3.84 mmol) was added to 3,6-di-t-butyl-fluorene (1.03 g, 3.73 mmol) in ether (20 ml) at −78° C. The reaction mixture was allowed to warm to room temperature and stirred for 3 h. 6-(4-tert-butyl-phenyl)-5-methyl-3-tert-butyl-fulvene (1.05 g, 3.74 mmol) in ether (5 ml) was added to the reaction mixture at −40° C. The reaction was stirred at room temperature for 2.5 h. The reaction mixture was quenched with water, extracted with ether, dried over $MgSO_4$, and evaporated under vacuum to afford the desired ligand. The ligand was washed with hot ethanol which resulted in 2.0 g of the bridged ligand or a yield of 95%.

The synthesis of (4-tert-Butyl-phenyl)-[(5-methyl-3-tert-butyl)3,6-di-tert-butyl-(fluorenyl)]methane zirconium dichloride was carried out as follows: Butyllithium (1.7 ml, 1.6M, 2.72 mmol) was added to (4-t-butyl)-[(5-methyl-3-tert-butyl)3,6-di-tert-butyl-(fluorenyl)]methane (0.71 g, 1.27 mmol) in ether (20 ml) at −78° C. The reaction mixture was allowed to heat to room temperature and the reaction was continued for 2.5 h. The solvent was removed under vacuum. $ZrCl_4$ (296 mg, 1.27 mmol) was added to the reaction mixture. Toluene (15 ml) was added at −40° C. and the reaction was stirred at room temperature overnight. The solvent was removed under vacuum.

Example 7

Bulk propylene polymerization with non-supported Catalyst E was conducted at 60° C. using a 2 L bench reactor. The results are summarized in Table 9.

TABLE 9

| # | Catalyst (mg) | $H_2$, ppm | Activity, g/g/cat/h | Tmelt, °C. | Tcryst, °C. | Mw/1000 | D | D' | % mmmm |
|---|---|---|---|---|---|---|---|---|---|
| 22* | 8.0 | 0 |  | 156.0 | 106.3 | 636.9 | 4.9 | 2.2 |  |
| 23 | 1.0 | 20 | 74,000 | 167.4 | 130.3 | 610.6 | 5.2 | 2.2 | 95.6 |
| 24 | 1.0 | 10 | 72,000 | 166.0 | 109.0 | 673.6 | 3.3 | 2.2 | 95.8 |

*10 x reactor

Catalyst E produced isotactic polypropylene with tacticity of 96% mmmm, Table 10, a melting temperature of 166-167° C., Table 11, and molecular weight of 670,000. The activity of 74,000 g/gCat/h was observed under an initial hydrogen concentration of 20 ppm.

TABLE 10

|  | # | |
|---|---|---|
|  | 23 | 24 |
| Recrystallization Peak | 130.300 | 108.966 |
| Delta H__Recrystallization | −70.639 | −79.080 |
| Second Melt Peak | 167.366 | 166.033 |
| Delta H__Second Melt | 58.622 | 54.491 |

TABLE 11

|  | # | |
|---|---|---|
|  | 23 | 24 |
| mmmm | 95.6 | 95.8 |
| mmmr | 1.4 | 1.3 |
| rmmr | 0.0 | 0.1 |
| mmrr | 1.6 | 1.4 |
| xmrx | 0.2 | 0.2 |
| mrmr | 0.0 | 0.0 |
| rrrr | 0.2 | 0.2 |
| rrrm | 0.3 | 0.3 |
| mrrm | 0.7 | 0.7 |
| % meso | 97.9 | 98.0 |
| % racemic | 2.1 | 2.0 |
| % error | 0.1 | 0.2 |
| def/1000 C. | 10.6 | 9.9 |

Example 8

Catalyst E was supported on G-952 silica with 2 wt % loading and tested in the 6-parallel reactor set. The results in terms of polymerization parameters and polymer properties are given in Table 12.

TABLE 12

| # | $H_2$, ppm | Activity, g/g/cat/h | Tm, °C. | Tc, °C. | Mw/1000 | Mw/Mn | Mz/Mw | % mmmm |
|---|---|---|---|---|---|---|---|---|
| 25 | 10 | 200 | 154.4 | 108.3 | 370.5 | 5.5 | 2.2 | ? |
| 26 | 20 | 260 | 155.0 | 111.0 | 292.9 | 3.3 | 2.0 | ? |
| 27 | 60 | 360 | 156.4 | 112.0 | 197.9 | 2.7 | 1.9 | ? |
| 28 | 65 | 433 | 156.4 |  | 267.7 | 3.7 | 2.1 | ? |
| 29 | 88 | 600 | 157.0 |  | 194.3 | 3.4 | 2.1 | ? |

Figure 3:
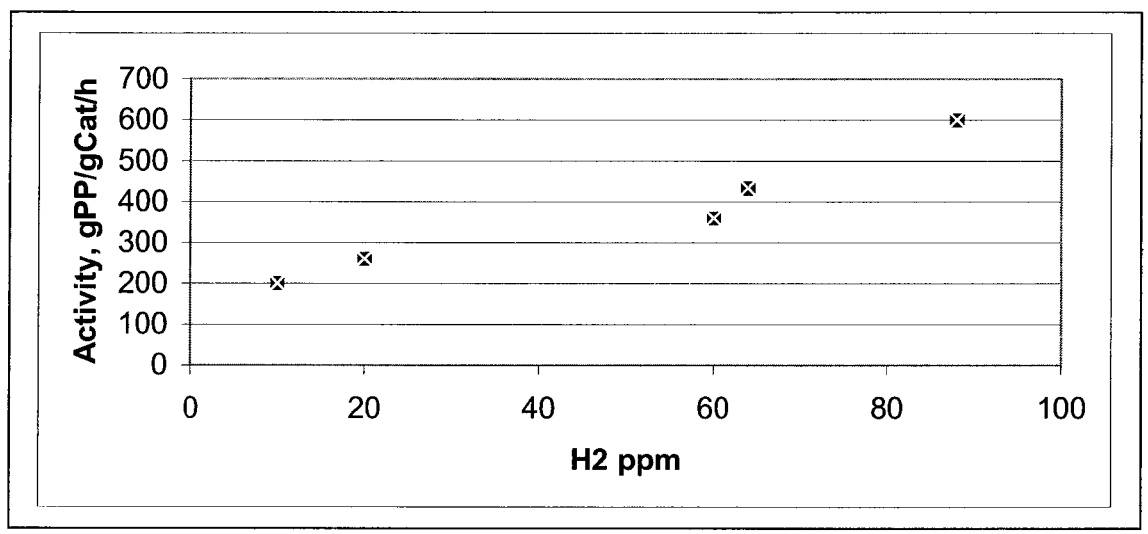
FIG. 3 is a plot of hydrogen concentration versus catalyst activity for Catalyst E.
Figure 4:
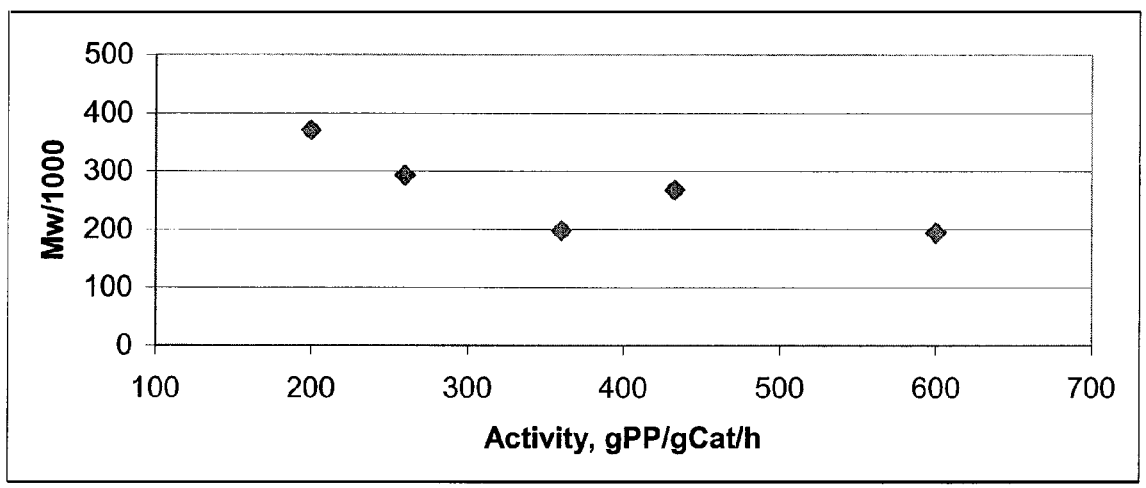
FIG. 4 is a plot of catalyst activity versus polymer molecular weight for Catalyst E.
Figure 5:
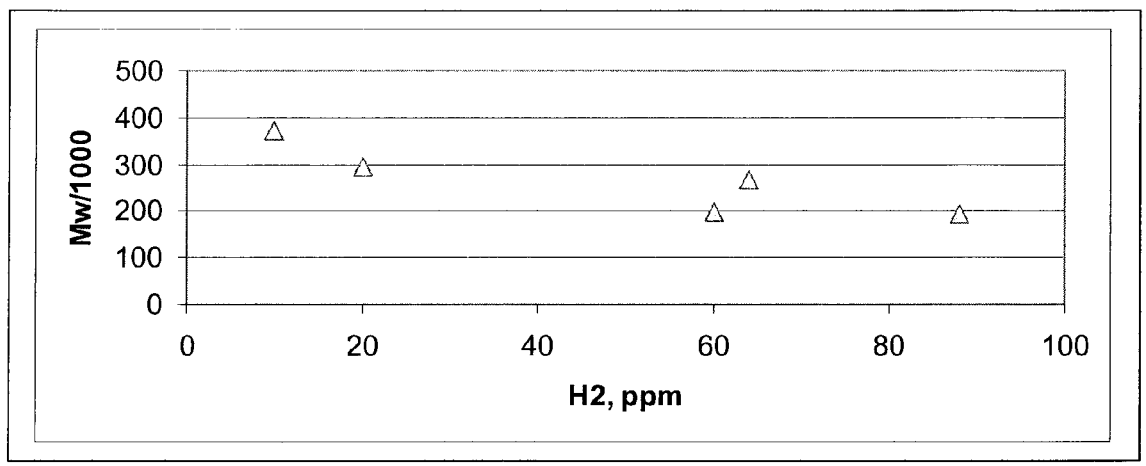
FIG. 5 is a plot of hydrogen concentration versus molecular weight of the polymer for Catalyst E.

The supported catalyst produced highly isotactic polypropylene with tacticity of 97% mmmm and melting temperature of 156-157° C. The molecular weight of polymers, produced by Catalyst G/G-952 depends on hydrogen concentrations and is in a range of 370,000-200,000 for polymerization at 88-100 ppm of $H_2$ as shown in FIGS. 3 and 4 respectively. The activity of the catalyst was 600 g/g/cat at 88 ppm of $H_2$, shown in FIG. 5.

Example 9

The ethylene/propylene copolymerization with Catalyst E supported on G-952 silica was conducted at 60° C. in 6×-parallel reactors under the initial hydrogen and ethylene concentrations indicated in Table 13. The results are also summarized in Table 13.

TABLE 13

| # | $H_2$, mmol | $C_2$, wt % in feed | Activity, g/g/cat/h | Tm, °C. | C2, w % in copo | MF, g/10 min | Mw/1000 | Mw/Mn | Mz/Mw |
|---|---|---|---|---|---|---|---|---|---|
| 30 | 88 | 0 | 600 | 157.0 | 0 | — | 194.3 | 3.4 | 2.1 |
| 31 | 88 | 0.5 | 687 | 145.7 | 2.3 | — | 106.6 | 2.9 | 1.9 |
| 32 | 88 | 1 | 707 | 135.7 | 3.1 | — | 86.7 | 2.9 | 1.9 |
| 33 | 88 | 1.5 | 733 | 128.4 | 4.5 |  | 81.2 | 2.3 | 1.8 |
| 34 | 65 | 0 | 433 | 156.4 | 0 | 16 | 267.7 | 3.7 | 2.1 |
| 35 | 65 | 0.5 | 567 | 144.0 | 2.5 | 75 | 136.3 | 3.3 | 2.0 |
| 36 | 65 | 1.0 | 687 | 136.0 | 4.3 | 200 | 94.4 | 2.6 | 1.8 |

Figure 6:
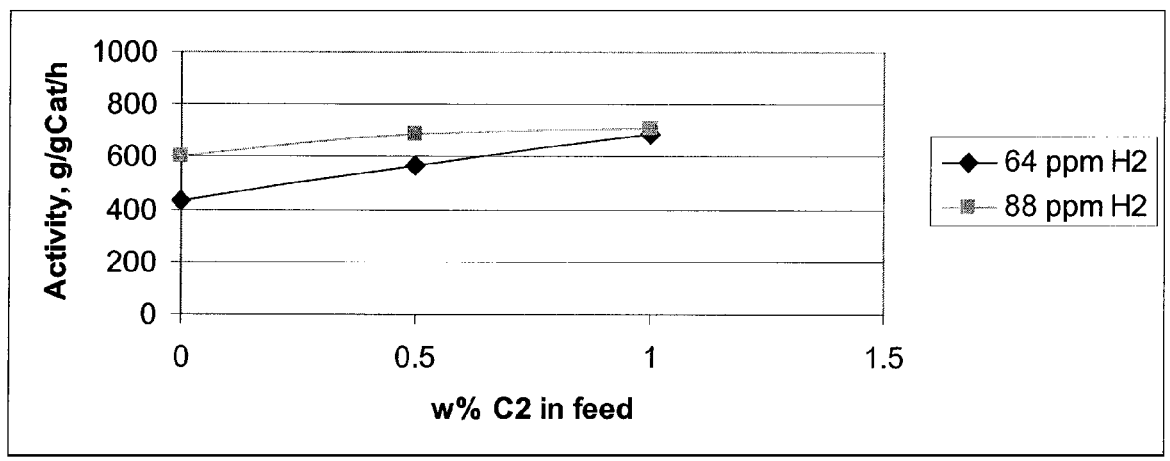
FIG. 6 is a plot of the concentration of ethylene in the feed versus catalyst activity for Catalyst E.
Figure 7:
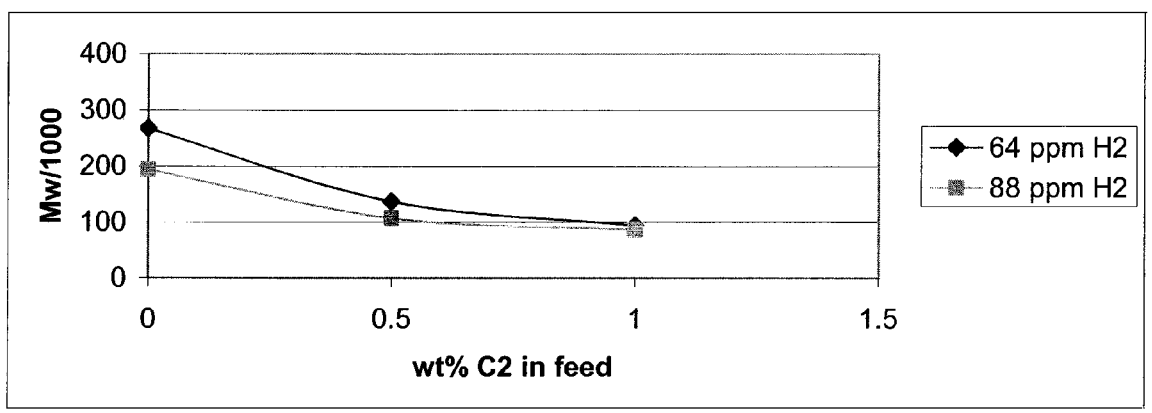
FIG. 7 is a plot the concentration of ethylene in the feed versus the polymer molecular weight for polymers produced using Catalyst E.
Figure 8:
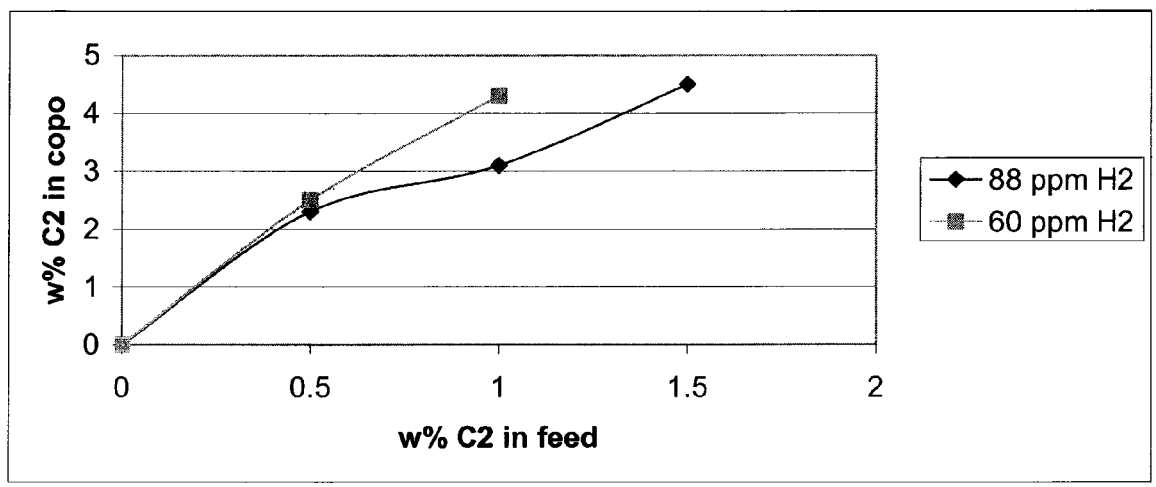
FIG. 8 is a plot of concentration of ethylene in the feed versus concentration of ethylene in the copolymer composition for polymers produced using Catalyst E.
Figure 10:
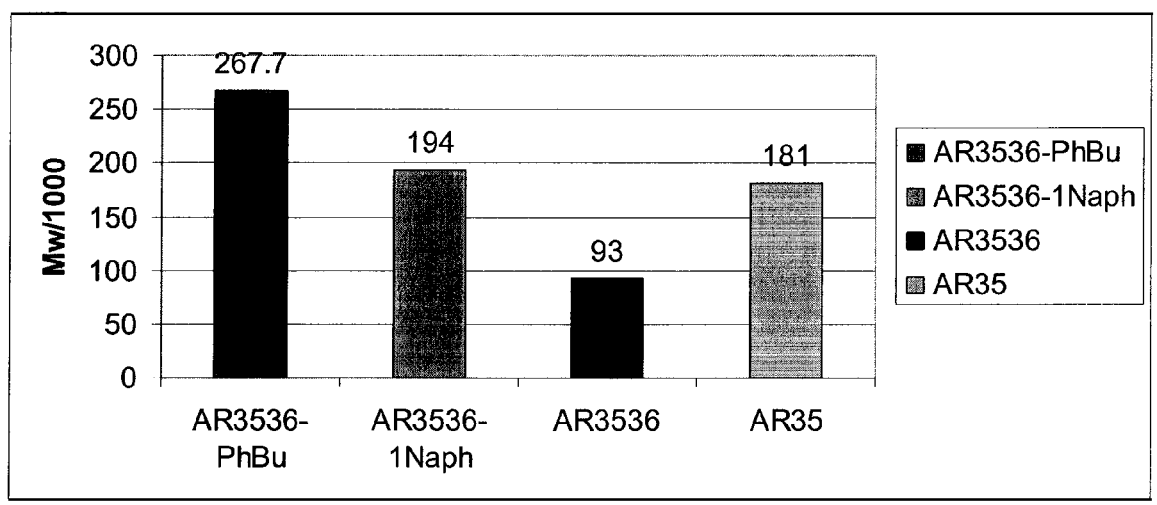
FIG. 10 is a plot of the comparative molecular weight of isotactic polypropylene produced by several different metallocene catalysts.
Figure 11:
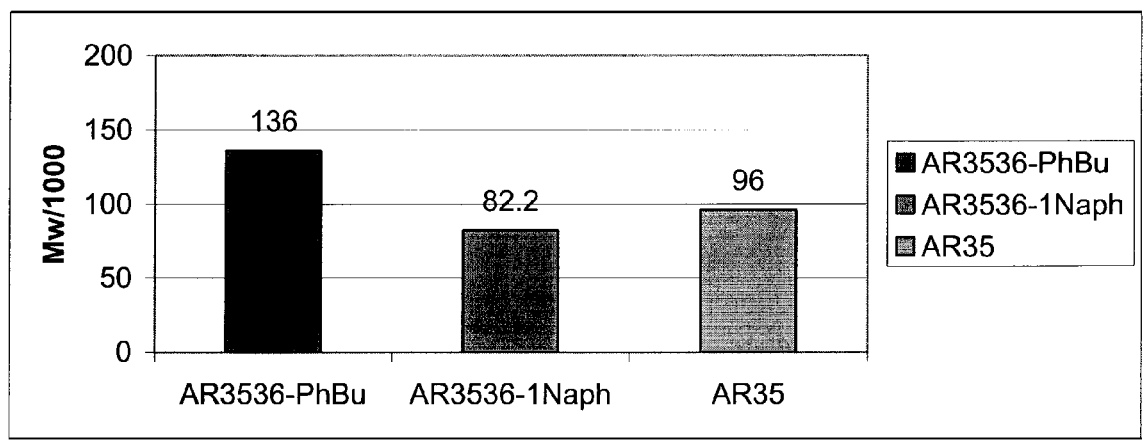
FIG. 11 is a plot of the comparative molecular weight of a random ethylene/propylene copolymer produced by several different metallocene catalysts.
Figure 12:
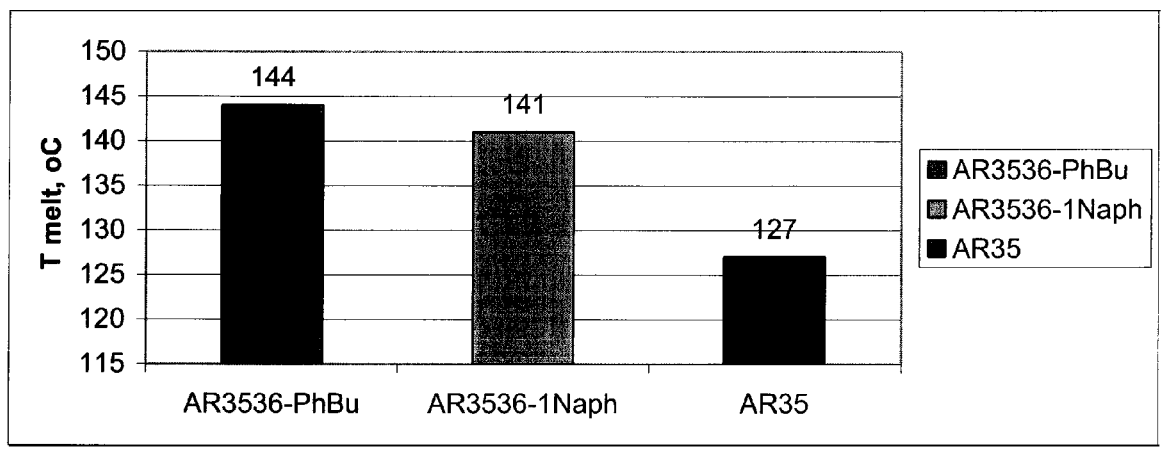
FIG. 12 is a plot of the comparative melting temperatures of a random ethylene/propylene copolymer produced by several different metallocene catalysts.

The results demonstrate that the catalyst activity increases with increasing ethylene concentration in feed under hydrogen concentration, FIG. 6, whereas the molecular weight decreased with an increasing ethylene concentration in the feed, FIG. 7. An activity of 733 g/gCat/h was observed at the initial hydrogen concentration of 88 ppm and ethylene concentration 1.5 wt %. The melt flow increased from 16 g/10 min to 200 g/10 min with increasing ethylene content in feed from 0 to 1.0 wt % for polymerization at 60 ppm of $H_2$. Catalyst E produced random copolymers (RCP) with ethylene contents of 4.3 wt % and melting point of 136° C. under polymerization with 60 ppm of hydrogen and 1.0 wt % ethylene in feed, FIG. 8. The tacticty of several samples of the RCP produced was determined and results are presented in Table 14.

ppm of $H_2$, shows that Catalyst E produces the highest molecular weight iPP (267,700) when compared with catalysts of the type exemplified by Catalyst A (194,000), Catalyst G (93,600) and Catalyst C (181,000). The activity of Catalyst E was 600 g/gCat/h (at 88 ppm of $H_2$) which was lower than for Catalysts A-C. The molecular weight of random copolymers produced with Catalyst A decreases with increasing ethylene content in feed which is similar to catalysts Catalysts G and C, see Table 15 and FIG. 10. The molecular weight of RCP with 2.5 wt % ethylene, is the highest for Catalyst E (Mw=136,000) when compared with Catalyst G (82,200) and Catalyst C, see FIG. 11. Catalyst E also produces a higher melting temperature RCP than Catalyst A and Catalyst C with the same ethylene content, see FIG. 12.

TABLE 15

| # | Catalyst (mg) | Polymer, g | Activity, g/g/cat/h | Tmelt, ° C. | Tcryst, ° C. | $Mn/10^3$ | $Mw/10^3$ | $Mz/10^3$ | D |
|---|---|---|---|---|---|---|---|---|---|
| 37 | E 8.0 mg | ? | ? | 156.0 | 106.3 | 129 | 637 | 1,392 | 4.9 |

TABLE 14

| | # | | | | |
|---|---|---|---|---|---|
| | 35 | 36 | 31 | 32 | 33 |
| mole % E | 3.7 | 6.3 | 3.4 | 4.6 | 6.6 |
| mole % P | 96.3 | 93.7 | 96.6 | 95.4 | 93.4 |
| wt % E | 2.5 | 4.3 | 2.3 | 3.1 | 4.5 |
| wt % P | 97.5 | 95.7 | 97.7 | 96.9 | 95.5 |
| mole % PP | 94.2 | 89.2 | 94.4 | 91.8 | 88.4 |
| mole % PE | 4.2 | 9.0 | 4.4 | 7.3 | 10.0 |
| mole % EE | 1.4 | 1.3 | 1.1 | 0.8 | 1.0 |
| mole % PPP | 86.5 | 78.1 | 85.7 | 82.5 | 78.6 |
| mole % PPE | 5.9 | 9.3 | 6.5 | 8.5 | 10.0 |
| mole % EPE | 3.8 | 6.3 | 4.4 | 4.4 | 4.9 |
| mole % PEP | 1.9 | 4.4 | 2.1 | 3.6 | 5.0 |
| mole % PEE | 0.8 | 1.0 | 0.6 | 0.6 | 1.0 |
| mole % EEE | 1.0 | 0.8 | 0.7 | 0.4 | 0.4 |
| num avg seq len of E | 1.1 | 1.1 | 1.1 | 1.1 | 1.1 |
| E 1 unit long | 48.0 | 64.1 | 59.6 | 74.7 | 68.8 |
| E 2 units long | 8.9 | 12.3 | 14.2 | 10.4 | 11.3 |
| E > 2 units long | 0.8 | 23.6 | 26.2 | 14.8 | 20.0 |
| P 1 unit long | 1.0 | 1.7 | 1.1 | 1.2 | 1.3 |
| P 2 units long | 1.0 | 2.5 | 1.6 | 2.4 | 3.4 |
| P > 2 units long | 98.0 | 95.8 | 97.3 | 96.4 | 95.3 |

Example 10

Figure 9:
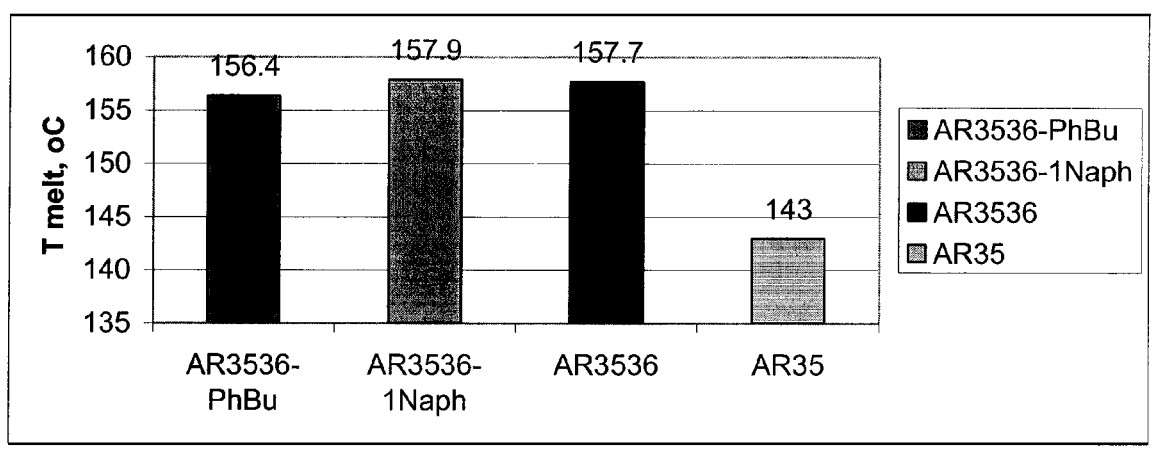
FIG. 9 is a plot of the comparative melting temperature of isotactic polypropylene produced by several different metallocene catalysts.

A comparison of polymerization behavior of Catalyst E with Catalyst A, Catalyst B and Catalyst C was made for homo propylene polymerization to produce isotactic polypropylene (iPP) at 60° C. and 60-70 ppm of $H_2$ concentration. The melting temperatures of iPP produced with Catalyst E were 156.4° C. This is close to the melting temperatures of iPP from Catalyst G and higher when compared with Catalyst C iPP (143° C.), FIG. 9. Catalyst G is characterized by a 3,6 symmetrically substituted Fl group, an unsubstituted Cp group and a napthyl bridging group. The tacticity of all catalysts having a 3,6-fluorenyl substitutent, is 96-97% mmmm. The molecular weight comparison for iPP produced at 60

A catalyst having a biphenyl substituted bridging ligand was synthesized. Specifically, (biphenyl)-[(5-methyl-3-tert-butyl)3,6-di-tert-butyl-(fluorenyl)]methane was synthesized by adding Butyllithium (3.8 ml, 1.6M in hexane, 6.08 mmol) to 3,6-di-t-butyl-fluorene (1.62 g, 5.87 mmol) in ether (20 ml) at −78° C. The reaction mixture was allowed to warm to room temperature and stirred for 5 h. Biphenyl-5-methyl-3-tert-butyl-fulvene (1.76 g, 5.87 mmol) in ether (20 ml) was added to the reaction mixture at −40° C. The reaction was stirred at room temperature overnight. The reaction mixture was quenched with water, extracted with ether, dried over $MgSO_4$, and evaporated under vacuum to afford the desired ligand. The ligand was washed with hot ethanol and crystallized from hexane/methylene chloride. The reaction yield was 1.2 g (35%). The metallated product, (biphenyl)-[(5-methyl-3-tert-butyl)3,6-di-tert-butyl-fluorenyl)]methane zirconium dichloride, hereafter referred to as Catalyst F, was produced by adding Butyllithium (2.0 ml, 1.6M, 3.20 mmol) to (biphenyl)-[(5-methyl-3-tert-butyl)3,6-di-tert-butyl-(fluorenyl)]methane (0.87 g, 1.51 mmol) in ether (20 ml) at −78° C. The reaction mixture was allowed to heat to room temperature and the reaction was continued for 5 h. The solvent was removed under vacuum. $ZrCl_4$ (352 mg, 1.51 mmol) was added to the reaction mixture. Toluene (15 ml) was added at −40° C. and the reaction was stirred at room temperature overnight. The solvent was removed under vacuum.

The ethylene/propylene copolymerization with Catalyst F supported on G-952 silica was conducted using 28 mg of catalyst at a polymerization temperature of 60° C. in 6×-parallel reactors at the indicated hydrogen and ethylene concentrations. The results in terms of polymerization activity and polymer properties are presented in Table 16.

TABLE 16

| # | H2, mmol | C$_2$, wt % in feed | Polymer, g | Activity, g/g/cat/h | Tm, °C | C2, w % | MF, g/10 min | Mw/1000 | Mw/Mn | Mz/Mw |
|---|---|---|---|---|---|---|---|---|---|---|
| 38 | 5.5 | 0   | 10.6 | 763   | 157.4 | 0   | 11.1 | 257.1 | 3.2 | 2.1 |
| 39 | 5.5 | 0.5 | 14.5 | 1,043 | 145.7 | 1.4 | 97.5 | 126.4 | 2.7 | 1.9 |
| 40 | 5.5 | 1.0 | 14.5 | 1,043 | 136.0 | 2.3 | 180  | 104.2 | 2.4 | 1.8 |
| 41 | 5.5 | 1.5 | 17.3 | 1,244 | 128.7 | 3.1 | 228  | 90.9  | 2.4 | 1.8 |
| 42 | 5.5 | 0.5 | 15.5 | 1,031 | 156.4 | —   | 73   | 130.1 | 2.6 | 1.9 |
| 43 | 5.5 | 1.5 | 10.8 | 720   | 155.0 | —   | 160  | 97.7  | 2.2 | 1.8 |

The results demonstrate that FMC catalysts of the type disclosed herein having tert-butyl substituents in the 3 and 6 positions of the Fl group and the monosubstitued bridging ligand polymer products of higher molecular weight and tacticity when compared to FMCs comprising an unsubstituted FMC (e.g., Catalyst C) or an FMC having tert-butyl substituents in the 3 and 6 positions and a disubstituted bridging ligand (e.g., Catalysts A and B). These results are summarized in Table 16a.

TABLE 16a

| | Catalyst | | | | |
|---|---|---|---|---|---|
| | F | E | A | G (Comparison) | C (Comparison) |
| T melt, °C | 157.4 | 156.4 | 157.9 | 157.7 | 143 |
| Tacticity, % mmmm | 97 | 97 | 97 | 97 | 90 |
| Mw/1000 | 251.1 | 267.7 | 194.0 | 93.0 | 181.0 |

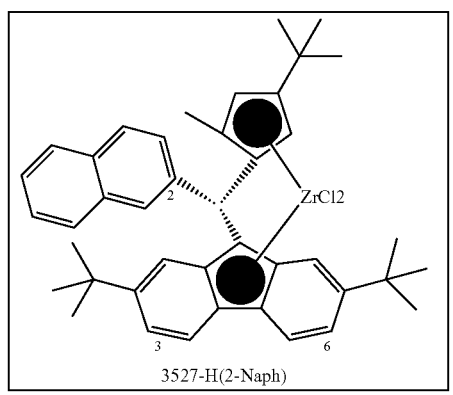

Structure XIX

3527-H(2-Naph)

Example 11

Catalysts useful in the production of isotactic polypropylene with a high molecular weight and a moderate melting temperature were synthesized. Catalysts H and I are characterized by a napthyl group as the bridging ligand, a symmetric 2,7 tert-butyl substitution of the fluorenyl group and a 5-methyl, 3-tert-butyl substitution of the cyclopentadienyl group. The structures of Catalysts H and I are given below by Structures XIX and XX respectively. The polymerization of propylene was carried out as described in Example 2 using these catalysts supported on G-952 silica in a parallel six-reactor set. Table 17 presents the results in terms of polymerization parameters and polymer properties for Catalysts H and I supported on G-952 silica which can be compared to the results observed with the use of Catalyst A under similar conditions given in Table 18.

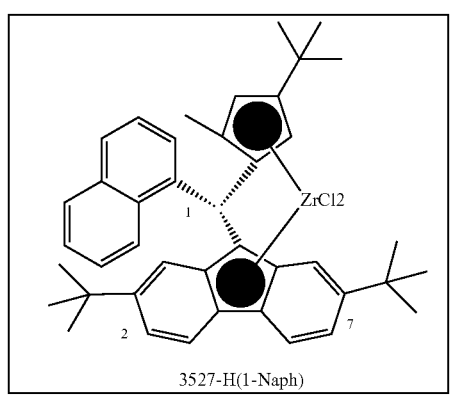

Structure XIX

3527-H(1-Naph)

TABLE 17

| # | Catalyst (mg) | H$_2$, ppm | Polymer, g | Activity, g/g/cat/h | Tm, °C. | Tc, °C. | Mw/1000 | Mw/Mn | Mz/Mw |
|---|---|---|---|---|---|---|---|---|---|
| 44 | 40 | 0 | 0.5 | 25 | 129.7 | 88.0 | 510.2 | 4.5 | 2.2 |
| 45 | 20 | 5 | 1.5 | 150 | 136.7 | 97.6 | 506.2 | 3.4 | 2.0 |
| 46 | 20 | 10 | 2.3 | 230 | 140.4 | 100.3 | 416.2 | 3.0 | 2.0 |
| 47 | 20 | 20 | 4 | 400 | 138.7 | 98.6 | 294.7 | 4.4 | 2.0 |
| 48 | 15 | 60 | 6 | 800 | 143.7 | 97.6 | 240.0 | 2.4 | 1.7 |

TABLE 18

| # | Catalyst (mg) | Polymer, g | Activity, g/g//h | Tm, °C. | Tc° C. | Mw | Mw/Mn | Mz/Mw |
|---|---|---|---|---|---|---|---|---|
| 49 | A (0.15 mg) | 0.9 | 12,000 | 133.7 | 87.3 | 763 | 5.5 | 2.2 |

Example 12

The ethylene/propylene copolymerization with Catalyst H supported on G-952 silica was conducted at 60° C. in 6×-parallel reactors in bulk propylene using 30 mg of catalyst and a 30 minute reaction time. The initial hydrogen concentration, ethylene concentration and results are summarized in Table 19.

TABLE 19

| # | H$_2$, ppm | wt % C$_2$ in feed | Polymer, g | Activity, g/g/cat/h | Tm, °C. | wt % C$_2$ in copo | MF, g/10 min | Mw/1000 | Mw/Mn | Mz/Mw | XS, % |
|---|---|---|---|---|---|---|---|---|---|---|---|
| 50 | 10 | 0.5 | 6.8 | 453 | 124.7 | 1.7 | 4.2 | 321.7 | 3.0 | 2.1 | 2.2 |
| 51 | 10 | 1 | 12 | 800 | 111.4 | 2.8 | 8.7 | 252.1 | 2.8 | 2.0 | 21.3 |
| 52 | 20 | 0.5 | 9.4 | 627 | 126.4 | 1.7 | 5.5 | 276.8 | 3.1 | 2.0 | 2.2 |
| 53 | 20 | 1 | 15.2 | 1013 | 111.4 | 2.9 | 9.4 | 228.0 | 2.8 | 1.8 | 19.2 |
| 54 | 40 | 0 | 1.7 | 113 | 138.7 | — | — | 250.2 | 3.4 | 2.1 | 0.8 |
| 55 | 40 | 0.5 | 6.5 | 433 | 128.7 | 2.4 | 12.7 | 222.3 | 3.1 | 2.0 | 2.5 |
| 56 | 40 | 1 | 8.3 | 553 | 112.0 | 2.9 | 14.7 | 196.0 | 2.5 | 1.8 | 19.1 |
| 57* | 60 | — | 6 | 800 | 143.7 | — | — | 240.0 | 2.4 | 1.7 | — |
| 58 | 60 | 0.5 | 5.4 | 360 | 127.0 | 1.9 | — | 176.4 | 2.8 | 1.9 | 2.5 |
| 59 | 60 | 0.5 | 10.5 | 700 | 127.4 | 1.5 | 63.6 | 156.1 | 2.9 | 1.9 | 2.6 |
| 60 | 60 | 1 | 16.5 | 1100 | 112.4 | 2.8 | 28.4 | 167.4 | 2.2 | 1.8 | 20.9 |
| 61 | 0 | 1 | 6 | 400 | 108 | 3.8 | 6.8 | 266.2 | 2.6 | 1.9 | 24.7 |

*= Reactions run using 15 mg of catalyst

Figure 13:
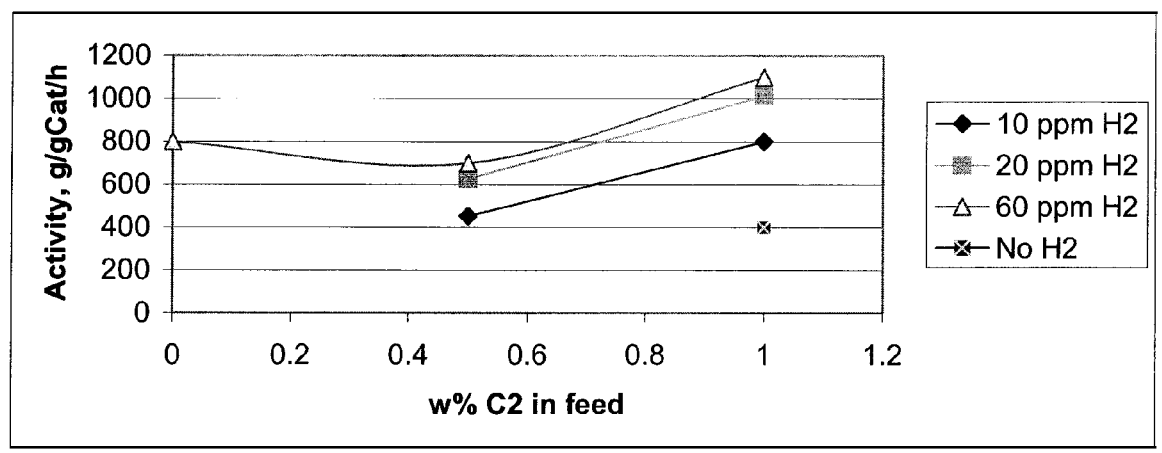
FIG. 13 is a plot of the concentration of ethylene in the feed versus catalyst activity for a random ethylene/propylene copolymer produced using Catalyst H.
Figure 14:
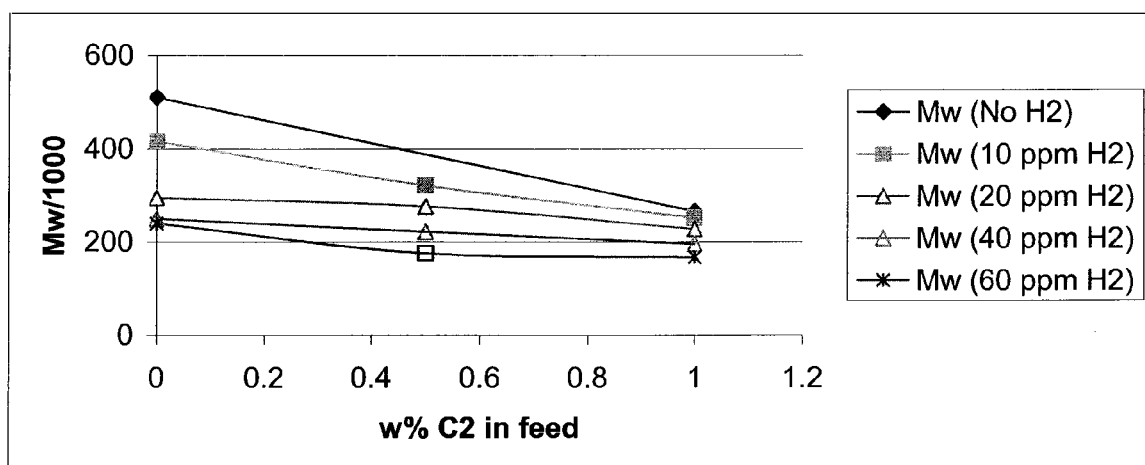
FIG. 14 is a plot of the concentration of ethylene in the feed versus the polymer molecular weight for a random ethylene/propylene copolymer produced using Catalyst H.
Figure 15:
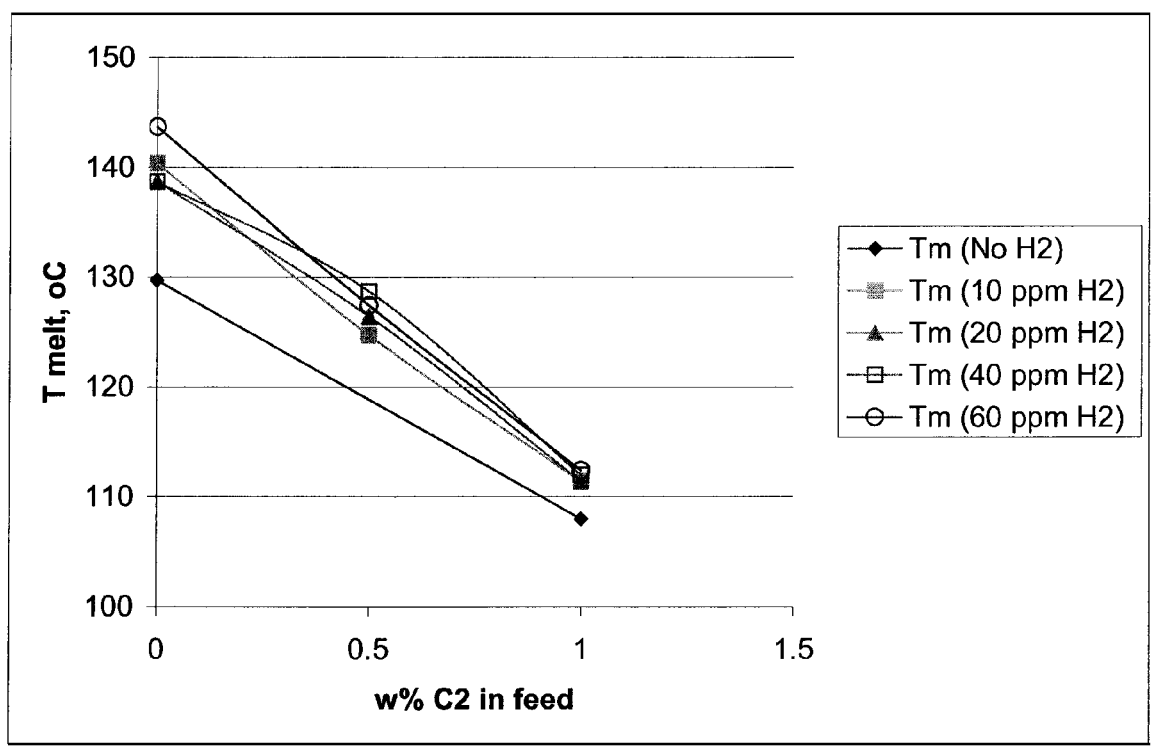
FIG. 15 is a plot of the concentration of ethylene in the feed versus the polymer melting temperature for a random ethylene/propylene copolymer produced using Catalyst H.
Figure 16:
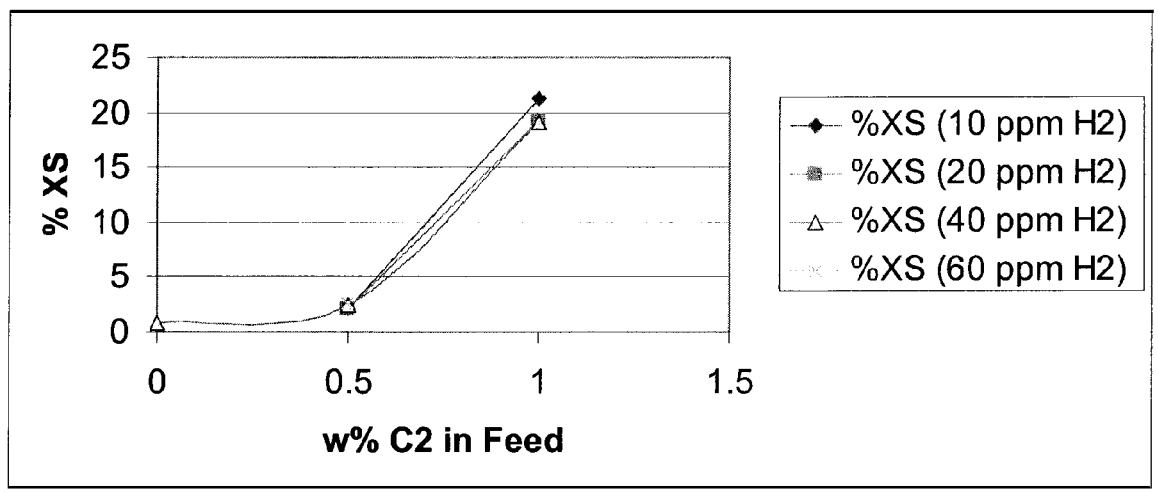
FIG. 16 is a plot of the concentration of ethylene in the feed versus the percent xylene solubles of the polymer composition for a random ethylene/propylene copolymer produced using Catalyst H.

In general, the activity of Catalyst H increases with increasing ethylene concentration in feed under the same concentration of hydrogen. The activity of 1,100 g/gCat/h was observed under the initial hydrogen concentration of 60 ppm and ethylene concentration of 1.0 wt %, see FIG. 13. The molecular weight slightly decreased with increasing ethylene content under the same initial hydrogen concentration, see FIG. 14. Catalyst H produced copolymers with melt flows under 15 g/10 min with ethylene contents of up to 3.0 wt % and melting points higher than 111° C. under polymerization with hydrogen concentration less than 40 ppm, see FIG. 15. The percent of xylene soluble fraction of homopolymer is less than 1% and dramatically increased with increasing ethylene content in copolymer higher than 1.5-2.0%, see FIG. 16.

$^{13}$C NMR was carried out on the copolymers produced by Catalyst H and the results are given in Tables 20a and 20b.

TABLE 20a

| | # | | | |
|---|---|---|---|---|
| | 50 | 51 | 52 | 53 |
| mole % E | 2.5 | 4.2 | 2.6 | 4.2 |
| mole % P | 97.5 | 95.8 | 97.4 | 95.8 |

TABLE 20a-continued

| | # | | | |
|---|---|---|---|---|
| | 50 | 51 | 52 | 53 |
| wt % E | 1.7 | 2.8 | 1.7 | 2.9 |
| wt % P | 98.3 | 97.2 | 98.3 | 97.1 |
| mole % PP | 95.3 | 92.0 | 95.5 | 92.0 |
| mole % PE | 4.4 | 7.6 | 4.0 | 7.5 |
| mole % EE | 0.5 | 0.5 | 0.7 | 0.6 |
| mole % PPP | 82.0 | 75.5 | 83.3 | 76.1 |
| mole % PPE | 10.5 | 14.4 | 9.9 | 14.1 |
| mole % EPE | 5.0 | 5.9 | 4.3 | 5.6 |
| mole % PEP | 1.9 | 3.6 | 1.8 | 3.5 |
| mole % PEE | 0.2 | 0.4 | 0.5 | 0.6 |
| mole % EEE | 0.5 | 0.3 | 0.4 | 0.2 |

TABLE 20b

|       | #              |                |
| Mole % | 50<br>1.7 wt % C$_2$ | 51<br>2.8 wt % C$_2$ |
| --- | --- | --- |
| PPP | 82.0 | 75.5 |
| PPE | 10.5 | 14.4 |
| EPE | 5.0  | 5.9  |
| PEP | 1.9  | 3.6  |
| PEE | 0.2  | 0.4  |
| EEE | 0.5  | 0.3  |

The $^{13}$C NMR indicates that copolymers produced by Catalyst H are dramatically enriched in ethylene compared to the feed composition. The EPE triad is more enriched than would be predicted from truly random copolymerization, therefore, Catalyst H has a tendency towards alternating copolymerization between ethylene and propylene, see Table 20a.

The results obtained using Catalyst H can be compared to that using Catalyst J the structure of which is shown in Structure XXI and the results of the copolymerization of ethylene and propylene in terms of polymerization activity of Catalyst J and polymer properties is given in Table 21.

Structure XXI

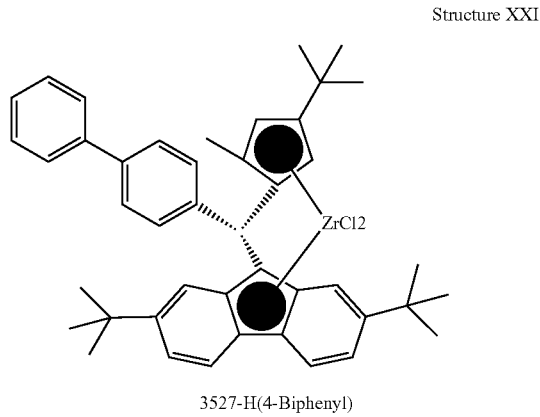

3527-H(4-Biphenyl)

Example 13

Catalysts useful in the production of isotactic polypropylene with a high to moderate molecular weight and a low melting temperature were synthesized. These catalysts exemplified by Catalyst K are characterized by a napthyl group as the bridging ligand, an unsubstituted fluorenyl group and a 5-methyl, 3-tert-butyl substitution of the cyclopentadienyl group. Catalyst K was prepared as follows:

Preparation of a fulvene, 6-(1-Naphthyl)-5-methyl-3-tert-butyl-fulvene was carried out by adding to a solution of methyl-tert-butylcyclopentadiene (4.35 g, 32.0 mmol) and 1-naphthaldehyde (5.0 g, 32.0 mmol)) in absolute ethanol (50 ml) small portions of sodium methoxide (4.5 g) under stirring and the mixture was stirred for 1 h. The reaction was quenched with water and extracted with ether. The solvents were evaporated under vacuum to give an orange liquid, which was purified by column chromatography. The chemical shift data from the $^1$H NMR are as follows: (silica gel, hexane/CH$_2$Cl$_2$=8/1) (Yield 4.4 g). $^1$H NMR (CDCl$_3$): δ 8.1, 7.9, and 7.6 (m, Naphth), 7.70 (s,1H, H-6), 6.36 and 6.02 (br s, 2H, H-Cp), 2.31 (s, 3H, Me), 1.23 (s, 9H, t-Bu). A second reaction to produce the fulvene was carried out. In this reaction, to a solution of methyl-tert-butylcyclopentadiene (4.64 g, 34.1 mmol) and 1-naphthaldehyde (5.32 g, 34.1 mmol)) in absolute ethanol (70 ml) was added a small portion of sodium methoxide (3.0 g, 55.5 mmol) under stirring and the mixture was stirred for 18 h. The reaction was quenched with water and extracted with ether. The solvents were evaporated under vacuum to give an orange liquid, which was purified by column chromatography (silica gel, hexane/CH$_2$Cl$_2$=8/1) (Yield 8.6 g, 91%).

Following the formation of the fulvene, addition of the fulvene to a substituted fluorenyl ligand was carried out to produce (1-Naphthyl)-[(5-methyl-3-tert-butyl)(fluorenyl)] methane. In this reaction butyllithium (5.5 ml, 1.6M in hexane, 8.8 mmol) was added to fluorene (1.44 g, 8.67 mmol) in ether (20 ml) at −78° C. The reaction mixture was allowed to warm to room temperature and stirred for 3 h. 6-(1-Naphthyl)-5-methyl-3-tert-butyl-fulvene (2.39 g, 8.66 mmol) in

TABLE 21

| # | T, °C. | H2, mmol | C$_2$, wt % in feed | Polymer, g | Activity, g/g/cat/h | Tm, °C. | MF, g/10 min | Mw/1000 | Mw/Mn | Mz/Mw |
| --- | --- | --- | --- | --- | --- | --- | --- | --- | --- | --- |
| 62 | 60 | 10  | 0   | 10  | 667 | 143.0 | —    | 142.4 | 2.6 | 1.9 |
| 63 | 70 | 10  | 0   | 9.6 | 640 | —     | —    | —     | —   | —   |
| 64 | 60 | 5.5 | 0   | 7.7 | 513 | —     | —    | 233.5 | 3.1 | 2.0 |
| 65 | 60 | 5.5 | 0.5 | 8.5 | 566 | —     | 20.5 | —     | —   | —   |
| 66 | 60 | 5.5 | 1.0 | 9.8 | 653 | 129.7 | 26.0 | 182.1 | 2.7 | 1.9 |
| 67 | 60 | 3.4 | 0   | 5.7 | 380 | 143.4 | 4.3  | 300.4 | 3.0 | 2.0 |
| 68 | 60 | 3.4 | 0.5 | 6.5 | 433 | 136.0 | 14.4 | 240.0 | 3.3 | 1.9 |
| 69 | 60 | 3.4 | 1.5 | 9   | 600 | 123.7 | 11.6 | 203.4 | 2.4 | 1.8 |
| 70 | 60 | 2.0 | 0   | 4   | 267 | —     | 2.8  | —     | —   | —   |
| 71 | 60 | 2.0 | 0   | 5   | 333 | 135.4 | —    | 314.1 | 3.5 | 2.1 |
| 72 | 60 | 2.0 | 0.5 | 6   | 400 | —     | 3.7  | —     | —   | —   |
| 73 | 60 | 2.0 | 1.0 | 7.6 | 507 | —     | 6.3  | —     | —   | —   |
| 74 | 60 | 2.0 | 1.5 | 9.5 | 633 | —     | 6.2  | —     | —   | —   |
| 75 | 60 | 2.0 | 1.5 | 7.3 | 487 | —     | 10.6 | —     | —   | —   | ether (5 ml) was added to the reaction mixture at −40° C. The reaction was stirred at room temperature for 2 h. The reaction mixture was quenched with water, extracted with ether, dried over MgSO$_4$, and evaporated under vacuum to afford the desired ligand. The ligand was purified by column chromatography (SiO$_2$, hexane/methylene chloride). A second reaction to form the bridged fulvene fluorenyl ligand was carried out. In this reaction butyllithium (7.6 ml, 1.6M in hexane, 12.2 mmol) was added to fluorene (1.94 g, 11.69 mmol) in ether (50 ml) at −78° C. The reaction mixture was allowed to warm to room temperature and stirred for 4 h. 6-(1-Naphthyl)-5-methyl-3-tert-butyl-fulvene (3.23 g, 11.7 mmol) in ether (10 ml) was added to the reaction mixture at −40° C. The reaction was stirred at room temperature for 3 h. The reaction mixture was quenched with water, extracted with ether, dried over MgSO$_4$, and evaporated under vacuum to afford the desired ligand. The ligand was purified by column chromatography (SiO$_2$, hexanes/methylene chloride (3.8 g, 75%). The $^1$H NMR in CDCl$_3$ was carried out and the chemical shift data is as follows: δ 8.1-6.6 (m, Flu, Naphth), 6.11 and 5.91 (s, 1H, H-Cp), 4.8 (m, 2H, H9-Flu and H-bridge), 2.8 (several br s, 2H, CH2-Cp), 1.69 and 1.65 (s, 3H, Me), 1.16 and 1.13 (s, 2.31 (s, 3H, Me), 1.23 (s, 9H, t-Bu).

Metallation of the bridged cyclopentadienyl fluorenyl ligand was carried out to produce (1-Naphthyl)-[(5-methyl-3-tert-butyl-cyclopentadienyl)(fluorenyl)]methane zirconium dichloride. In this reaction butyllithium (3.1 ml, 1.6M, 4.96 mmol) was added to (1-naphthyl)-[(5-methyl-3-tert-butyl)(fluorenyl)]methane (1.07 g, 2.42 mmol) in ether (20 ml) at −78° C. The reaction mixture was allowed to heat to room temperature and the reaction was continued for 3 h. The solvent was removed under vacuum. ZrCl$_4$ (563 mg, 2.42 mmol) was added to the reaction mixture. Toluene (15 ml) was added at −40° C. and the reaction was stirred at room temperature overnight. The solvent was removed under vacuum. The structure of Catalyst K is given by Structure XXII.

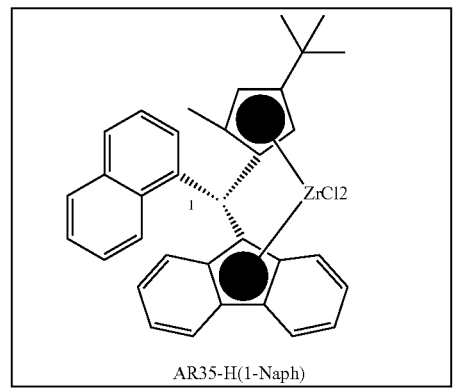

Structure XXII

AR35-H(1-Naph)

Example 14

A homogeneous polymerization reaction using Catalyst K was conducted in bulk propylene in 10× Multi-Clave reactor at 60° C. The catalyst was used without purification. The polymerization behavior for Catalyst K is listed in Table 22.

TABLE 22

| # | Catalyst (mg) | Polymer, g | Activity, g/g//h | Tm, °C. | Tc° C. | Mw | Mw/Mn | Mz/Mw |
|---|---|---|---|---|---|---|---|---|
| 76 | K (0.16) | 1.3 | 16,250 | 131.0 | 94.0 | 322.8 | 3.2 | 2.1 |

Catalyst K produced a polymer with a melting point of 131° C. and a molecular weight of 333,000.

Example 15

Catalyst K was supported on G-952 silica with 2 wt % loading and tested in the 6-parallel reaction set. Polymerization data for Catalyst J/G-952 is shown in Table 23.

TABLE 23

| # | Catalyst (mg) | H$_2$, ppm | Polymer, g | Activity, g/g/cat/h | Tm, °C. | Tc, °C. | MF, | Mw/1000 | Mw/Mn | Mz/Mw |
|---|---|---|---|---|---|---|---|---|---|---|
| 77 | 20 | 0 | 2 | 200 | 132.4 | 95.3 | — | 347.0 | 5.3 | 2.3 |
| 78 | 15 | 10 | 6 | 800 | 139.7 | 100.0 | 3.8 | 365.3 | 2.9 | 2.0 |
| 79 | 15 | 20 | 8 | 1,070 | 140.4 | 101.3 | 11.7 | 264.8 | 3.9 | 2.0 |
| 80 | 15 | 60 | 10 | 1,330 | 142.0 | 102.6 | 15.9 | 181.1 | 2.7 | 1.9 |

Figure 17:
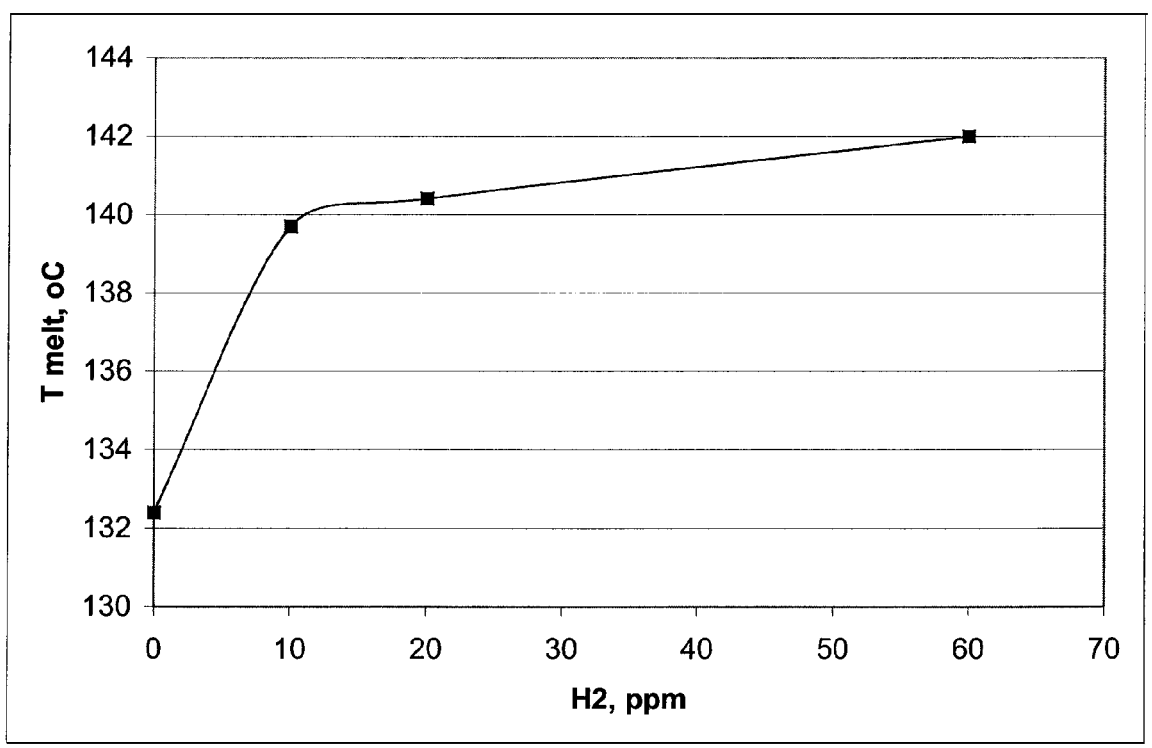
FIG. 17 is a plot of the effect of the hydrogen concentration on the melting points of the polymers produced using Catalyst K.
Figure 18:
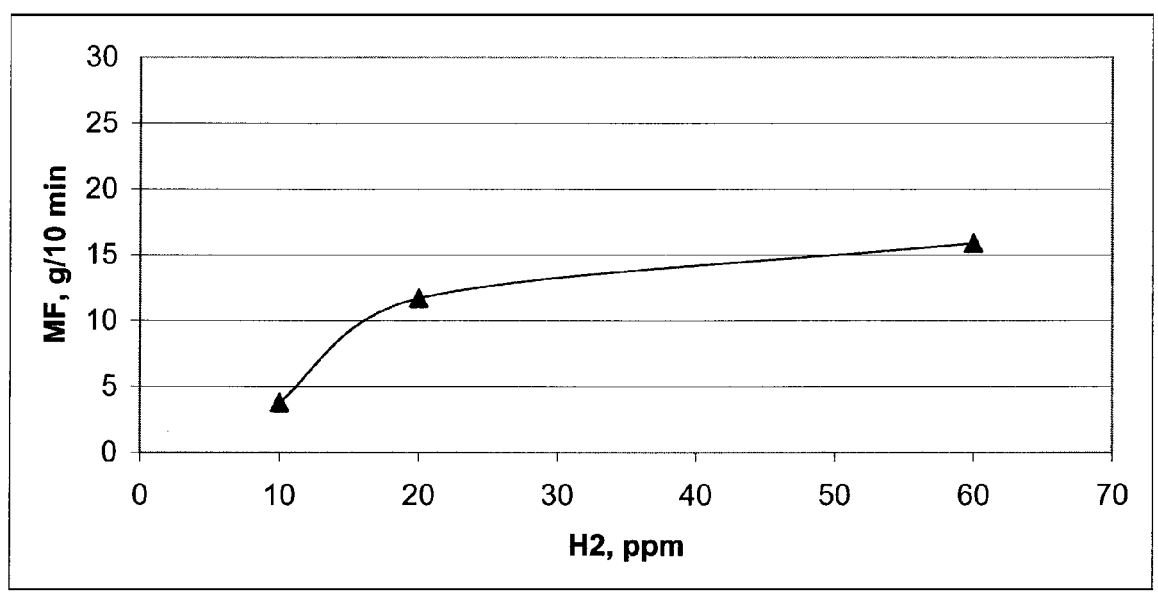
FIG. 18 is a plot of the effect of the hydrogen concentration on the melt flow of the polymer produced using Catalyst K.

The catalyst produced polymers with melting temperatures in the range of 132-142° C. under polymerization at 60° C. and hydrogen concentrations of 0-60 ppm. The melting point of the polymer is observed to increase with increasing a hydrogen concentration, see FIG. 17. The melt flow rate appears to plateau with increasing hydrogen concentration, see FIG. 18 while the molecular weight decreases with increasing hydrogen concentration as shown in Table 23. At the highest $H_2$ concentration, 60 ppm, the polymer produced had a melt flow rate of 16 g/10 min. The observed activity at this condition was around 1,300 g/gCat/h. The catalyst produced isotactic polypropylene with % mmmm of 80-83 as shown in Table 24.

TABLE 24

| | # | |
|---|---|---|
| | 79 | 80 |
| mmmm | 82.5 | 80.0 |
| mmmr | 5.4 | 5.8 |
| rmmr | 0.5 | 0.4 |
| mmrr | 5.4 | 6.5 |

TABLE 24-continued

| | # | |
|---|---|---|
| | 79 | 80 |
| xmrx | 1.0 | 1.4 |
| mrmr | 0.5 | 0.0 |
| rrrr | 0.8 | 1.2 |
| rrrm | 1.0 | 1.4 |
| mrrm | 2.8 | 3.2 |
| % meso | 92.0 | 90.2 |
| % racemic | 8.0 | 9.8 |
| % error | 1.0 | 1.1 |
| def/1000 C. | 5.2 | 5.6 |

Example 16

The ethylene/propylene copolymerization with Catalyst K supported on G-952 silica was conducted at 60° C. in 6×-parallel reactors under different initial hydrogen and ethylene concentration. The results are summarized in Table 25.

TABLE 25

| # | $H_2$, ppm | $C_2$, wt % in feed | Polymer, g | Activity, g/g/cat/h | Tm, ° C. | C2, w % | MF, g/10 min | Mw/1000 | Mw/Mn | Mz/Mw | % XS |
|---|---|---|---|---|---|---|---|---|---|---|---|
| 81 | 10 | 0 | 6 | 400 | 124.7 | 0 | 6.6 | 264.0 | 3.1 | 2.1 | — |
| 82 | 10 | 0.5 | 10 | 666,7 | 122.7 | 2.0 | 6.4 | 239.5 | 2.8 | 2.0 | 10.4 |
| 83 | 10 | 1.0 | 19.2 | 1280 | 112.7 | 3.3 | 14.1 | 204.9 | 3.4 | 2.1 | 18.0 |
| 84 | 20 | 0 | 8 | 1,070 | 140.4 | 0 | 11.7 | 264.8 | 3.9 | 2.0 | — |
| 85 | 20 | 0.5 | 15.8 | 1,053 | 127.7 | 1.8 | 11.1 | 236.6 | 2.9 | 2.0 | 10.1 |
| 86 | 20 | 1.0 | 20 | 1,333 | 112.7 | 3.2 | 14.7 | 192.7 | 2.8 | 1.9 | 17.9 |
| 87 | 60 | 0 | 10 | 1,330 | 142.0 | 0 | 15.9 | 181.1 | 2.7 | 1.9 | — |
| 88 | 60 | 0.5 | 18.2 | 1,213 | 128.7 | 1.8 | 35.4 | 167.1 | 3.0 | 2.0 | 12.1 |
| 89 | 60 | 1.0 | 26 | 1,733 | 116.0 | 2.9 | 26.0 | 151.0 | 4.2 | 2.0 | 16.9 |
| 90 | 0 | 1.0 | 12.5 | 833 | 112.4 | 3.4 | 11.1 | 209.0 | 3.3 | 2.0 | 23.4 |
| 91 | 0 | 3 | 18 | 900 | — | — | 60.7 | — | — | — | — |

Figure 19:
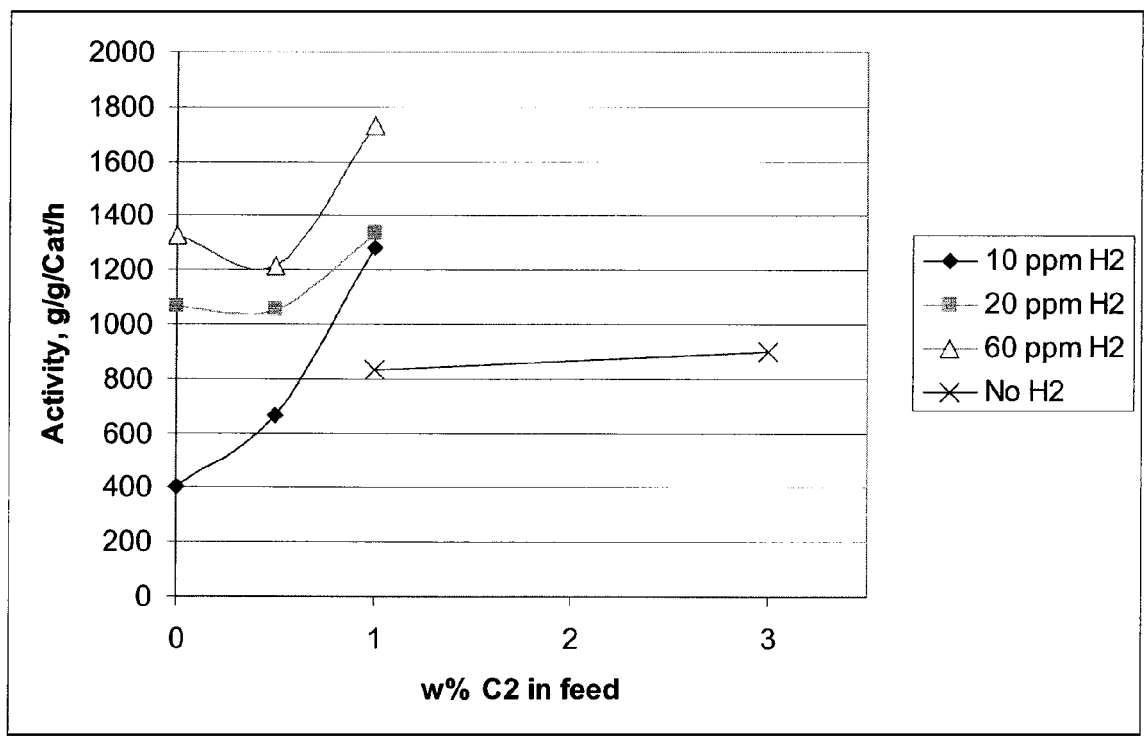
FIG. 19 is a plot of ethylene concentration in the feed versus the catalyst activity for an ethylene/propylene random copolymer produced using Catalyst K.
Figure 20:
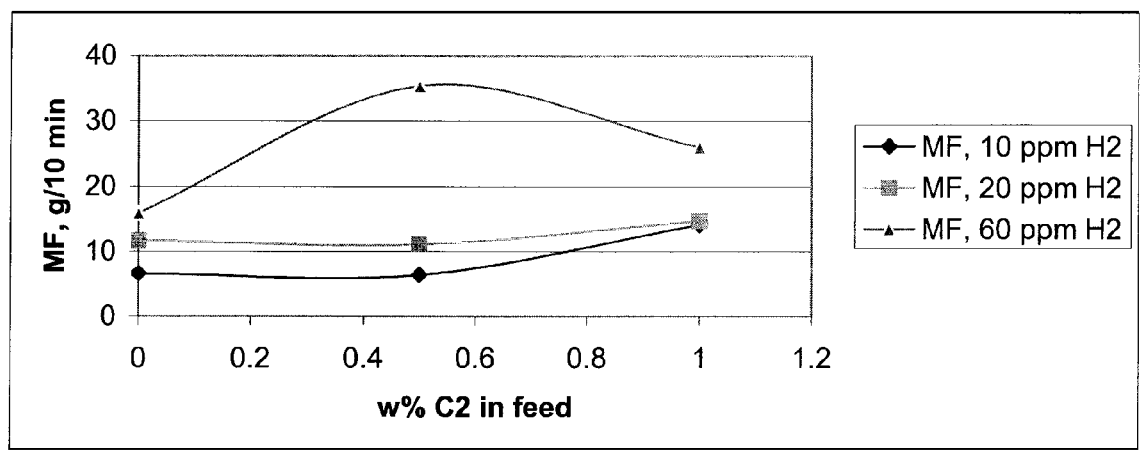
FIG. 20 is a plot of the ethylene concentration in the feed versus the melt flow of the polymeric composition for an ethylene/propylene random copolymer produced using Catalyst K.
Figure 21:
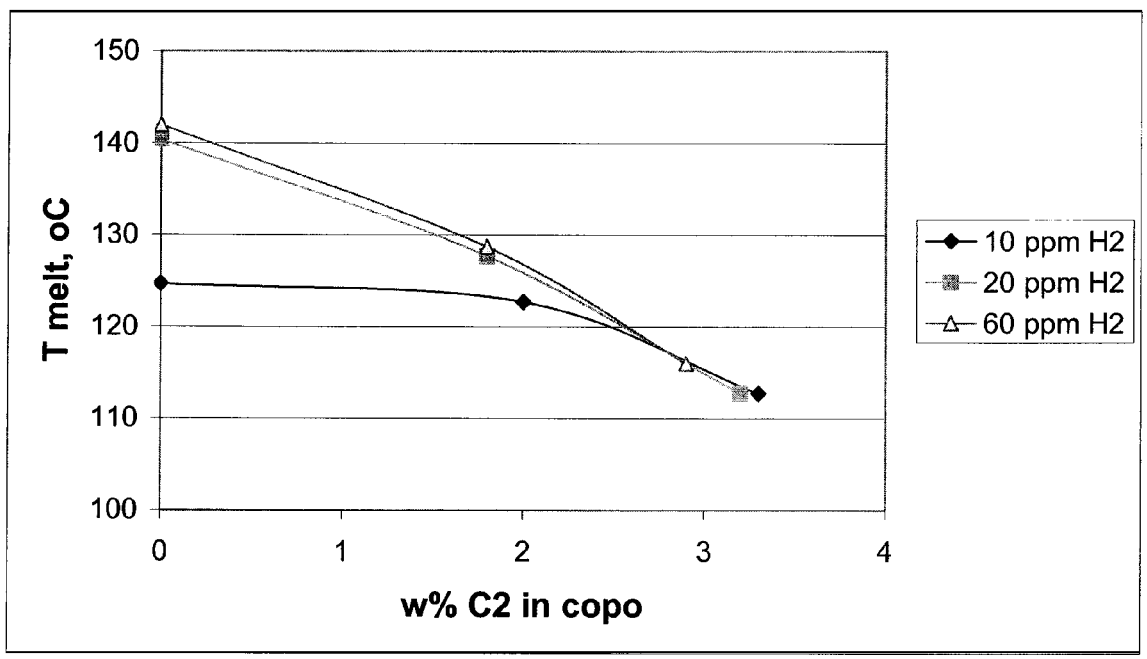
FIG. 21 is a plot of the ethylene concentration in the polymeric composition versus the melting temperature of the polymer for an ethylene/propylene random copolymer produced using Catalyst K.
Figure 22:
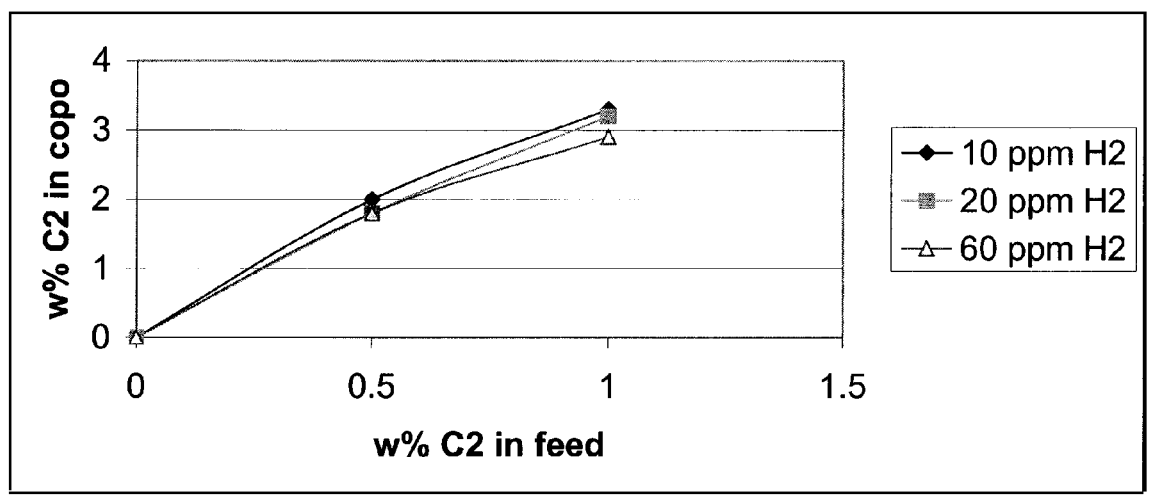
FIG. 22 is a plot of the ethylene concentration in the feed versus the ethylene concentration in the polymeric composition for an ethylene/propylene random copolymer produced using Catalyst K.

The results demonstrate that in general, the catalyst activity increased with increasing ethylene concentration in feed under the same concentration of hydrogen. Under initial hydrogen concentration of 10 ppm, the activity increases by three times when ethylene concentration in feed increased from 0 to 1.0 wt %. The activity of 1,700 g/gCat/h was observed under the initial hydrogen concentration of 60 ppm and ethylene concentration 1.0 wt %, see FIG. 19. The melt flow slightly increased with increasing ethylene content under the same initial hydrogen concentration, see FIG. 20. The catalyst produced copolymers with melt flows under 14 g/10 min with ethylene contents up to 3.3 wt % and melting points higher than 112° C., see FIGS. 21 and 22 respectively.

$^{13}C$ NMR was run on several of the copolymers produced by Catalyst K and the results are shown in Table 26.

TABLE 26

| | Mole % # | | | | | |
|---|---|---|---|---|---|---|
| | 2.0 wt % E 82 10 ppm | 1.8 wt % E 85 20 ppm | 1.8 wt % E 88 60 ppm | 3.3 wt % E 83 10 ppm | 3.2 wt % E 86 20 ppm | 2.9 wt % E 89 60 ppm |
| PPP | 78.2 | 80.0 | 78.8 | 72.5 | 72.9 | 74.3 |
| PPE | 12.6 | 11.6 | 12.0 | 15.5 | 15.2 | 14.5 |
| EPE | 6.2 | 5.7 | 6.4 | 7.2 | 7.2 | 6.8 |

TABLE 26-continued

| | Mole % # | | | | | |
|---|---|---|---|---|---|---|
| | 2.0 wt % E 82 10 ppm | 1.8 wt % E 85 20 ppm | 1.8 wt % E 88 60 ppm | 3.3 wt % E 83 10 ppm | 3.2 wt % E 86 20 ppm | 2.9 wt % E 89 60 ppm |
| PEP | 2.7 | 2.2 | 2.2 | 4.1 | 4.1 | 3.9 |
| PEE | 0.2 | 0.4 | 0.4 | 0.7 | 0.6 | 0.5 |
| EEE | 0.3 | 0.1 | 0.2 | 0.2 | 0.2 | 0.1 |

The $^{13}$C NMR indicates that copolymer produced by Catalyst K is dramatically enriched in ethylene compared to the feed composition, see Table 25 and FIG. 28. The sequence distribution analysis of PE copolymers produced by Catalyst K is presented in Table 26. The EPE triad is more enriched than would be predicted from truly random copolymerization, therefore, Catalyst K has a tendency towards alternating copolymerization between ethylene and propylene. The same effect was observed for other Cp-Flu catalysts (see Angew. Chem., Int. Ed. Engl., 1998, 37, 922; Macromol. Rapid Commun., 1998, 19, 337; J. Am. Chem. Soc., 2001, 123, 9555).

These results can be compared to the results obtained when Catalyst J was used, the structure of this catalyst is given in Structure XXIII.

Structure XXIII

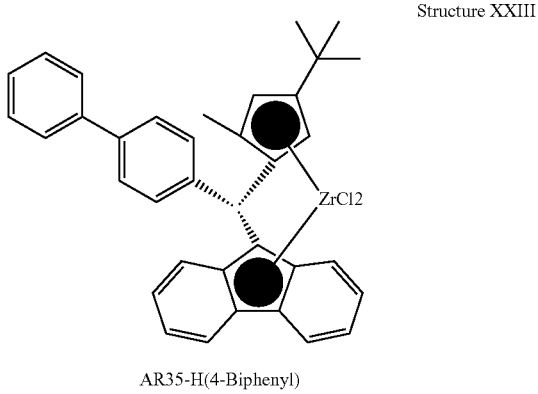

AR35-H(4-Biphenyl)

The synthesis of Catalyst J began with the production of (4-Bi-phenyl)-[(5-methyl-3-tert-butyl)(fluorenyl)]methane. Specifically, butyllithium (6.3 ml, 1.6M in hexane, 10.1 mmol) was added to fluorene (1.63 g, 9.82 mmol) in ether (50 ml) at −78° C. The reaction mixture was allowed to warm to room temperature and stirred for 4 h. 6-(4-Bi-phenyl)-5-methyl-3-tert-butyl-fulvene (2.95 g, 9.83 mmol) in ether (20 ml) was added to the reaction mixture at −40° C. The reaction was stirred at room temperature for 2 h. The reaction mixture was quenched with water, extracted with ether, dried over MgSO$_4$, and evaporated under vacuum to afford the desired ligand. The ligand was then washed with hot ethanol (4.0 g, 87%).

(4-Biphenyl)-[(5-methyl-3-tert-butyl-cyclopentadienyl) (fluorenyl)]methane zirconium dichloride was then synthesized. Specifically, butyllithium (3.2 ml, 1.6M, 5.12 mmol) was added to (4-biphenyl)-[(5-methyl-3-tert-butyl)(fluorenyl)]methane (1.15 g, 2.47 mmol) in ether (20 ml) at −78° C. The reaction mixture was allowed to heat to room temperature and the reaction was continued for 3 h. The solvent was removed under vacuum. ZrCl$_4$ (570 mg, 2.44 mmol) was added to the reaction mixture. Toluene (15 ml) was added at −40° C. and the reaction was stirred at room temperature overnight. The solvent was removed under vacuum to afford a crude complex (1.5 g). Finally, the FMC (4-Biphenyl)-[(5-methyl-3-tert-butyl-cyclopentadienyl) (fluorenyl)]methane zirconium dichloride was prepared. Specifically, butyllithium (3.3 ml, 1.6M, 5.28 mmol) was added to (4-biphenyl)-[(5-methyl-3-tert-butyl)(fluorenyl)]methane (1.17 g, 2.51 mmol) in ether (20 ml) at −78° C. The reaction mixture was allowed to heat to room temperature and the reaction was continued overnight. The solvent was removed under vacuum. ZrCl$_4$ (584 mg, 2.51 mmol) was added to the reaction mixture. Ether (20 ml) was added at −60° C. and the reaction was stirred at room temperature for 5 hs. The solution was concentrated and the solution was filtered to afford a solid. The solid was washed with hexane, and crystallized from methylene chloride/hexane to afford the desired orange complex (0.65 g, 37%).

The ethylene/propylene copolymerization with Catalyst J supported on G-952 silica was conducted at 60° C. for 30 minutes in 6×-parallel reactors using 30 mg of catalyst under the initial hydrogen and ethylene concentration indicated in Table 27. The results are also summarized in Table 27.

TABLE 27

| # | H$_2$, mmole | wt % C$_2$ in feed | Polymer, g | Tm, ° C. | MF, g/10 min | Mw/1000 | Mw/Mn | Mz/Mw |
|---|---|---|---|---|---|---|---|---|
| 92 | 5.5 | 0 | 7 | 138.7 | 2.5 | 326.9 | 4.9 | 2.2 |
| 93 | 3.4 | 0 | 5.5 | 138.0 | 1.1 | 409.8 | 3.3 | 2.0 |
| 94 | 3.4 | 0.5 | 8.0 | 129.4 | 5.4 | 245.1 | 2.6 | 1.8 |
| 95 | 3.4 | 1.0 | 3.6 | 123.4 | 8.4 | 218.9 | 2.4 | 1.8 |
| 96 | 2.0 | 0 | 4.5 | — | 0.8 | 467.2 | 3.8 | 2.0 |
| 97 | 2.0 | 0.5 | 6.5 | 127.0 | 3.1 | 286.2 | 2.3 | 1.8 |
| 98 | 2.0 | 1.0 | 10 | 120.7 | 7.4 | 258.5 | 2.3 | 1.8 |

The results demonstrate that FMC catalysts of the type disclosed herein having either unsubstituted Fl groups or Fl groups with tert-butyl substituents in the 2 and 7 and a mono-substituted bridging group produced high molecular weight, low melt flow ethylene/propylene copolymers.

The embodiments having been generally described, the preceding examples are given as particular embodiments and to demonstrate the practice and advantages thereof. It is understood that the examples are given by way of illustration and are not intended to limit the specification of the claims in any manner.

While embodiments have been shown and described, modifications thereof can be made by one skilled in the art without departing from the spirit and teachings of the disclosure. The embodiments described herein are exemplary only, and are not intended to be limiting. Many variations and modifications of the embodiments disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from 1 to 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. An olefin polymerization process comprising contacting one or more olefins and a catalyst component in a reaction zone under suitable reaction conditions to form a polyolefin, wherein the catalyst component is characterized by the formula:

B(Cp)(Fl)MQ$_2$ wherein M comprises a metal, Q is a halogen, an alkyl group or an aryl group or combinations thereof, Cp is a cyclopentadienyl group substituted with a tertiary butyl group in the 3-position, Fl is a fluorenyl group, B is a bridging group that may be characterized by the general formula —YRH wherein Y is C and R comprises an alkyl group, an aryl group, a poly-aryl group or combinations thereof.

2. The process of claim 1 wherein the polyolefin is polypropylene, polyethylene, a copolymer of propylene, or a copolymer of ethylene.

3. The process of claim 1 further comprising contacting a co-catalyst in said reaction zone.

4. The process of claim 3 wherein the catalyst component and the co-catalyst are supported.

5. The process of claim 1 wherein the catalyst component is further characterized by the formula:

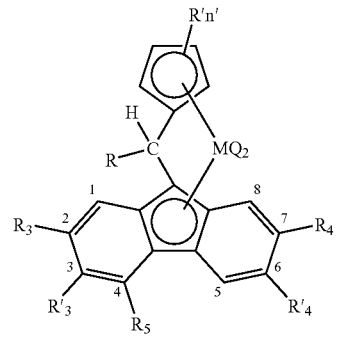

wherein R' is a C$_1$-C$_4$ alkyl group, a cyclic group, an aryl group or combinations thereof, n' is 1 to 4, M is titanium, zirconium or hafnium, Q is a halogen, alkyl group, aryl group or combination thereof and R$_3$, R$_4$, R'$_3$, or R'$_4$ may be the same or different and each is hydrogen, a methyl group, an isopropyl group, a tertiary butyl group, a phenyl group, a substituted phenyl group or combinations thereof, R$_5$ is hydrogen, an alkyl group, an aromatic group or combinations thereof, and R is an alkyl group, an aryl group, a poly-aryl group or combinations thereof.

6. The process of claim 5 wherein R is a methyl group, phenyl group, 2-methyl-phenyl group, 4-methyl-phenyl group, 2,6-dimethyl-phenyl group, 2,4,6-trimethyl-phenyl group, 4-tert-butyl-phenyl group, 2,6-dimethyl-4-tert-butyl-phenyl group, 2,6-diisopropyl-phenyl group, 2,6-diisopropyl-4-tert-butyl-phenyl group, 1-naphthyl group, 1-naphthyl group containing alkyl and aryl substituents, 2-naphthyl group containing alkyl and aryl substituents, 4-biphenyl group, 2-biphenyl group, 1-anthracenyl group, 9-anthracenyl group, or phenanthrenyl group.

7. The process of claim 5 wherein the catalyst component is further characterized by one of the following formulas A, C, and E:

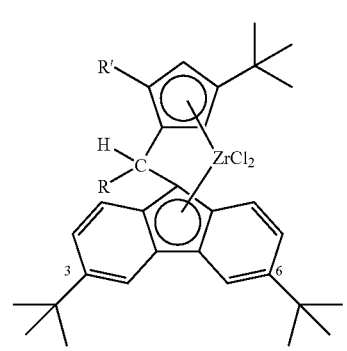

A

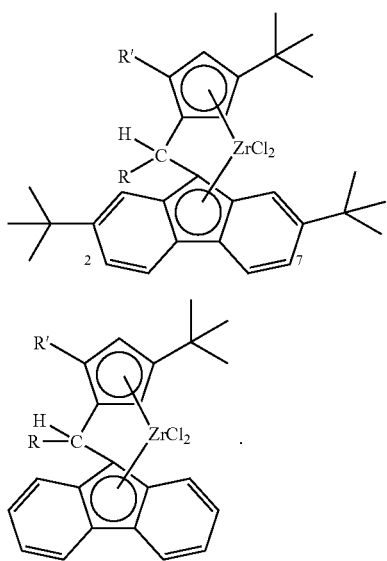

8. The process of claim 7 wherein the catalyst component is characterized by formula A and R' is hydrogen or a methyl group and R is a methyl group, phenyl group, 2-methyl-phenyl group, 4-methyl-phenyl group, 2,6-dimethyl-phenyl group, 2,4,6-trimethyl-phenyl group, 4-tert-butyl-phenyl group, 2,6-dimethyl-4-tert-butyl-phenyl group, 2,6-diisopropyl-phenyl group, 2,6-diisopropyl-4-tert-butyl-phenyl group, 1-naphthyl group, 1-naphthyl group containing alkyl and aryl substituents, 2-naphthyl group containing alkyl and aryl substituents, 4-biphenyl group, 2-biphenyl group, 1-anthracenyl group, 9-anthracenyl group, or phenanthrenyl group.

9. The process of claim 7 wherein the catalyst component is characterized by formula C and R' is hydrogen or a methyl group and R is a methyl group, phenyl group, 2-methyl-phenyl group, 4-methyl-phenyl group, 2,6-dimethyl-phenyl group, 2,4,6-trimethyl-phenyl group, 4-tert-butyl-phenyl group, 2,6-dimethyl-4-tert-butyl-phenyl group, 2,6-diisopropyl-phenyl group, 2,6-diisopropyl-4-tert-butyl-phenyl group, 1-naphthyl group, 1-naphthyl group containing alkyl and aryl substituents, 2-naphthyl group containing alkyl and aryl substituents, 4-biphenyl group, 2-biphenyl group, 1-anthracenyl group, 9-anthracenyl group, or phenanthrenyl group.

10. The process of claim 7 wherein the catalyst component is characterized by formula E and R' is hydrogen or a methyl group and R is a methyl group, phenyl group, 2-methyl-phenyl group, 4-methyl-phenyl group, 2,6-dimethyl-phenyl group, 2,4,6-trimethyl-phenyl group, 4-tert-butyl-phenyl group, 2,6-dimethyl-4-tert-butyl-phenyl group, 2,6-diisopropyl-phenyl group, 2,6-diisopropyl-4-tert-butyl-phenyl group, 1-naphthyl group, 1-naphthyl group containing alkyl and aryl substituents, 2-naphthyl group containing alkyl and aryl substituents, 4-biphenyl group, 2-biphenyl group, 1-anthracenyl group, 9-anthracenyl group, or phenanthrenyl group.

* * * * *